US006410539B1

(12) United States Patent
Arnould

(10) Patent No.: US 6,410,539 B1
(45) Date of Patent: Jun. 25, 2002

(54) IMIDAZOLE DERIVATIVES AND THEIR USE AS FARNESYL PROTEIN TRANSFERASE INHIBITORS

(75) Inventor: Jean-Claude Arnould, Reims (FR)

(73) Assignees: Astrazenca UK Limited, London (GB); Zeneca Pharma SA, Cergy Cedex (FR)

( * ) Notice: Subject to any disclaimer, the term of this patent is extended or adjusted under 35 U.S.C. 154(b) by 0 days.

(21) Appl. No.: 09/509,476

(22) PCT Filed: Oct. 19, 1998

(86) PCT No.: PCT/GB98/03115

§ 371 (c)(1),
(2), (4) Date: Mar. 24, 2000

(87) PCT Pub. No.: WO99/20612

PCT Pub. Date: Apr. 29, 1999

(30) Foreign Application Priority Data

Oct. 22, 1997 (EP) ............................................. 97402503
Oct. 22, 1997 (EP) ............................................. 97402504

(51) Int. Cl.⁷ ...................... A61K 31/50; C07D 401/00; C07D 421/00; C07D 277/20
(52) U.S. Cl. ............................ 514/252.05; 514/253.09; 514/256; 514/326; 514/397; 514/402; 544/238; 544/333; 544/366; 546/210; 548/202; 548/214; 548/255; 548/262.2
(58) Field of Search .................. 514/252.05, 253.09, 514/256, 326, 397, 402; 544/238, 333, 366; 546/210; 548/314.7, 202, 214, 255, 262.2

(56) References Cited

U.S. PATENT DOCUMENTS

| | | | | |
|---|---|---|---|---|
| 4,100,152 A | * | 7/1978 | Fujino et al. ............. 260/112.5 |
| 4,221,803 A | | 9/1980 | Nardi et al. ................. 424/273 |
| 4,324,792 A | * | 4/1982 | Bradshaw et al. .......... 424/267 |
| 4,518,607 A | | 5/1985 | Walker ........................ 514/399 |
| 5,238,922 A | | 8/1993 | Graham et al. ................ 514/18 |
| 5,326,773 A | | 7/1994 | de Solms et al. ........... 514/336 |
| 5,340,828 A | | 8/1994 | Graham et al. ............. 514/357 |
| 5,352,705 A | | 10/1994 | Deana et al. ................ 514/630 |
| 5,478,934 A | * | 12/1995 | Yuan et al. .................. 540/546 |
| 5,534,537 A | | 7/1996 | Ciccarone et al. .......... 514/397 |

FOREIGN PATENT DOCUMENTS

| | | |
|---|---|---|
| EP | 0 534 546 A1 | 3/1993 |
| EP | 0 696 593 A2 | 2/1995 |
| WO | WO 95/25086 | 9/1995 |
| WO | 96 30015 | 10/1996 |
| WO | WO 96/37204 | 11/1996 |
| WO | WO 97/06138 | 2/1997 |
| WO | 97 17070 | 5/1997 |
| WO | WO 98/32741 | 7/1998 |

OTHER PUBLICATIONS

James et al.; "Benzodiazepine Peptidomimetics: Potent Inhibitors of Ras Farnesylation in Animal Cells"; Science, vol. 260, Jun. 1993, pp. 1937–1942.
Leftheris et al.: "Development of highly potent inhibitors of ras farnesyltransferase possessing cellular and in vivo activity"; Journal of Medicinal Chemistry, vol. 39, No. 1, 1996 pp. 224–236, XP00210847.
Lerner et al.: "Ras CAAX Petpidomimetric FTI–277 Selectively Blocks Oncogenic . . . Inactive Ras–Fat Complexes"; The Journal of Biological Chemistry, vol. 270, Nov. 1995, pp. 26802–26806.
Reiss et al.; "Inhibition of Purified p21$^{ras}$ Farnesyl:Protein Trasnferase by Cys–AAX Tetrapetpides"; Cell, vol. 62, Jul. 1990, pp. 81–88.
Williams et al.; "2–Substituted piperazines as constrained amino acids. Application to the synthesis of potent, non carboxylic acid inhibitors of farnesyltransferase."Journal of Medicinal Chemistry., vol. 39, No. 7, –1996, pp. 345–1348, XP002101848.

* cited by examiner

*Primary Examiner*—Mukund J. Shah
*Assistant Examiner*—Tamthom N. Truong
(74) *Attorney, Agent, or Firm*—Morgan, Lewis & Bockius LLP

(57) ABSTRACT

The present invention relates to a compound of Formula (1) wherein $Ar^1$ represent (A) or (B) or (C); $R^1$ is hydrogen, $C_{1-4}$alkyl or $C_{1-4}$alkanoyl; $R^{12}$ and $R^{13}$ are independently hydrogen or $C_{1-4}$alkyl; $Ar^2$ is phenyl or heteroaryl; p is 0 or 1; $Ar^3$ is of formula (I) wherein W, X, Y and Z are independently CH or N, provided that at least two of W, X, Y and Z are CH and $R^2$ and —$(CH_2)_nR^3$ are attached to ring carbon atoms; $R^2$ is a group of Formula (II) or $R^2$ represents a lactone of Formula (III) the group of Formula (II) or (III) having L or D configuration at the chiral alpha carbon in the corresponding free amino acid; n is 0, 1 or 2; $R^3$ is phenyl or heteroaryl; provided that: when n is 0, $Ar^3$ is substituted by $R^2$ in the 4-position and —$(CH_2)_nR^3$ in the 3- or 5-position; and when n is 1 or 2, $Ar^3$ is substituted by $R^2$ in the 3- or 5-position and —$(CH_2)_nR^3$ in the 4-position; and $R^5$–$R^9$, m and n are as defined in the specification; or a pharmaceutically-acceptable salt, prodrug or solvate thereof. Processes for their preparation, their use as therapeutic agents and pharmaceutical compositions containing them. A particular use is in cancer therapy.

12 Claims, No Drawings

IMIDAZOLE DERIVATIVES AND THEIR USE AS FARNESYL PROTEIN TRANSFERASE INHIBITORS

This application is the national phase of international application PCT/G98/03115 filed Oct. 19, 1998 which designated the U.S.

This invention relates to compounds that inhibit farnesylation of mutant ras gene products through inhibition of the enzyme farnesyl-protein transferase (FPTase). The invention also relates to methods of manufacturing the compounds, pharmaceutical compositions and methods of treating diseases, especially cancer, which are mediated through farnesylation of ras.

Cancer is believed to involve alteration in expression or function of genes controlling cell growth and differentiation. Whilst not wishing to be bound by theoretical considerations the following text sets out the scientific background to ras in cancer. Ras genes are frequently mutated in tumours. Ras genes encode guanosine triphosphate (GTP) binding proteins which are believed to be involved in signal transduction, proliferation and malignant transformation. H-, K- and N-ras genes have been identified as mutant forms of ras (Barbacid M, Ann. Rev. Biochem. 1987, 56: 779–827). Post translational modification of ras protein is required for biological activity. Farnesylation of ras catalysed by FPTase is believed to be an essential step in ras processing. It occurs by transfer of the farnesyl group of farnesyl pyrophosphate (FPP) to a cysteine at the C-terminal tetrapeptide of ras in a structural motif called the CAAX box. After further post-translational modifications, including proteolytic cleavage at the cysteine residue of the CAAX box and methylation of the cysteine carboxyl, ras is able to attach to the cell membrane for relay of growth signals to the cell interior. In normal cells activated ras is believed to act in conjunction with growth factors to stimulate cell growth. In tumour cells it is believed that mutations in ras cause it to stimulate cell division even in the absence of growth factors (Travis J, Science 1993, 260: 1877–1878), possibly through being permanently in GTP activated form rather than cycled back to GDP inactivated form. Inhibition of farnesylation of mutant ras gene products will stop or reduce activation.

One class of known inhibitors of farnesyl transferase is based on farnesyl pyrophosphate analogues; see for example European patent application EP 534546 from Merck. Inhibitors of farnesyl tansferase based on mimicry of the CAAX box have been reported. Reiss (1990) in Cell 62, 81–8 disclosed tetrapeptides such as CVIM (Cys-Val-Ile-Met). James (1993) in Science 260 1937–1942 disclosed benzodiazepine based peptidomimetic compounds. Lerner (1995) in J. Biol. Chem. 270, 26802 and Eisai in International Patent Application WO 95/25086 disclosed further peptidomimetic compounds based on Cys as the first residue. Bristol-Myers Squibb in European Patent Application EP 696593 disclosed farnesyl transferase inhibitors having a 4-sulfanylpyrrolidine residue in the first position.

According to one aspect of the present invention there is provided a compound of Formula (1):

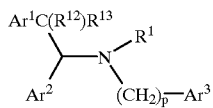

Formula (1)

wherein $Ar^1$ represents:

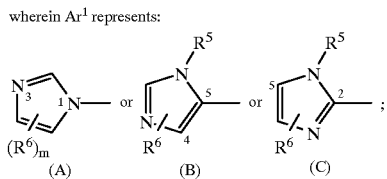

$R^5$ is hydrogen, $C_{1-4}$alkyl, phenyl$C_{1-4}$alkyl;
$R^6$ is hydrogen, $C_{1-4}$alkyl, hydroxy$C_{1-4}$alkyl, halo$C_{1-4}$alkyl, dihalo$C_{1-4}$alkyl, $C_{1-4}$alkoxy, $C_{1-4}$alkoxy$C_{1-4}$alkyl, sulfanyl$C_{1-4}$alkyl, amino$C_{1-4}$alkyl, N—($C_{1-4}$alkyl)amino$C_{1-4}$alkyl, N,N-di-($C_{1-4}$alkyl)amino$C_{1-4}$alkyl or phenyl$C_{1-4}$alkyl;
m is 0,1 or 2;
$R^1$ is hydrogen, $C_{1-4}$allyl or $C_{1-4}$alkanoyl;
$R^{12}$ and $R^{13}$ are independently hydrogen or $C_{1-4}$alkyl;
$Ar^2$ is phenyl or heteroaryl;
p is 0 or 1;
$Ar^3$ is of the formula:

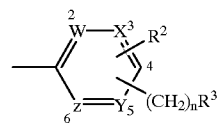

wherein W, X, Y and Z are independently is CH or N, provided that at least two of W, X, Y and Z are CH and $R^2$ and $—(CH_2)_nR^3$ are attached to ring carbon atoms; $R^2$ is a group of the Formula (2):

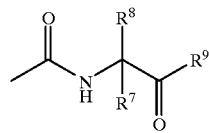

Formula (2)

wherein $R^7$ is hydrogen or $C_{1-4}$alkyl, $R^8$ is $—(CH_2)_q—R^{10}$ wherein q is 0–4 and $R^{10}$ is $C_{1-4}$alkylsulfanyl, $C_{1-4}$alkylsulfinyl, $C_{1-4}$alkylsulfonyl, hydroxy, $C_{1-4}$alkoxy, carbamoyl, N—$C_{1-4}$alkylcarbamoyl, N,N-(di$CC_{1-4}$alkyl)carbamoyl, $C_{1-4}$alkyl, phenyl, thienyl, or $C_{1-4}$alkanoylamino; $R^9$ is hydroxy, $C_{1-6}$-alkoxy, $C_{3-9}$-cycloalkyloxy, heterocyclyloxy, heterocyclyl$C_{1-4}$alkoxy or $—NH—SO_2—R^{11}$ wherein $R^{11}$ represents, trifluoromethyl, $C_{1-4}$alkyl, phenyl, heteroaryl, aryl$C_{1-4}$alkyl or heteroaryl$C_{1-4}$alkyl; or $R^2$ represents a lactone of Formula (3)

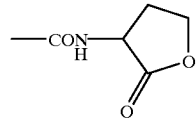

Formula (3)

the group of Formula (2) or (3) having L or D configuration at the chiral alpha carbon in the corresponding free amino acid;
n is 0, 1 or 2;
$R^3$ is phenyl or heteroaryl;
phenyl and heteroaryl rings in $R^3$, $R^5$, $R^6$, $R^9$, $R^{11}$ and $Ar^2$ are independently optionally substituted on ring carbon atoms by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, thiol, $C_{1-4}$alkylsulfanyl, $C_{1-4}$alkylsulfinyl, $C_{1-4}$alkylsulfonyl, $C_{1-4}$alkanesulphonamido, $\underline{N}$—($C_{1-4}$alkylsulphonyl)—$\underline{N}$—$C_{1-4}$alkylamino, aminosulfonyl, $\underline{N}$—($C_{1-4}$alkyl)aminosulfonyl, $\underline{N},\underline{N}$-di($C_{1-4}$alkyl)aminosulfonyl, carbamoyl, $\underline{N}$-($C_{1-4}$alkyl)carbamoyl, $\underline{N},\underline{N}$-(di$C_{1-4}$alkyl)carbamoyl, carbamoyl$C_{1-4}$alkyl, $\underline{N}$-($C_{1-4}$alkyl)carbamoyl$C_{1-4}$alkyl, $\underline{N},\underline{N}$-(di$C_{1-4}$alkyl)carbamoyl$C_{1-4}$alkyl, hydroxy$C_{1-4}$alkyl and $C_{1-4}$alkoxy$C_{1-4}$alkyl and on ring NH groups by $C_{1-4}$alkyl, $C_{1-4}$alkanoyl, $C_{1-4}$alkylsulfonyl, halo$C_{1-4}$alkyl, difluoromethyl or trifluoromethyl;

provided that:

when n is 0, $Ar^3$ is substituted by $R^2$ in the 4-position and —$(CH_2)_nR^3$ in the 3- or 5-position; and when n is 1 or 2, $Ar^3$ is substituted by $R^2$ in the 3- or 5-position and —$(CH_2)_nR^3$ in the 4-position;

or a pharmaceutically-acceptable salt, prodrug or solvate thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula (1) defined above may exist in optically active or racemic forms by virtue of one or more asymmetric carbon atoms, the invention includes in its definition any such optically active or racemic form which possesses the property of inhibiting FTPase. The synthesis of optically active forms may be carried out by standard techniques of organic chemistry well known in the art, for example by synthesis from optically active starting materials or by resolution of a racemic form. Similarly, inhibitory properties against FTPase may be evaluated using the standard laboratory techniques referred to hereinafter.

The term "heterocyclyl" refers to a 5- or 6-membered monocyclic ring containing 1 to 3 heteroatoms selected from nitrogen, oxygen and sulfur. The term "heteroaryl" refers to a 5–10 membered monocyclic heteroaryl ring containing upto 3 heteroatoms selected from nitrogen, oxygen and sulphur.

The term "halogen" refers to fluorine, chlorine, bromine and iodine. The term "carbamoyl" refers to —$C(O)NH_2$. The term "BOC" refers to tert-butoxycarbonyl.

Examples of $C_{1-4}$alkyl include methyl, ethyl, propyl isopropyl, sec-butyl and tert-butyl; examples of $C_{1-4}$alkoxy include methoxy, ethoxy and propoxy; examples of $C_{1-4}$akanoyl include formyl, acetyl and propionyl; examples of $C_{1-4}$alkanoyloxy include acetyloxy and propionyloxy; examples of $C_{1-4}$alkylamino include methylamino, ethylamino, propylamino, isopropylamino, sec-butylamino and tert-butylamino; examples of di-($C_{1-4}$alkyl)amino include di-methylamino, di-ethylamino, and $\underline{N}$-ethyl-$\underline{N}$-methylamino; examples of $C_{1-4}$alkanoylamino include acetamido and propionylamino; examples of $C_{1-4}$alkoxycarbonyl include methoxycarbonyl, ethoxycarbonyl and propoxycarbonyl; examples of $C_{1-4}$alkylsulfanyl include methylsulfanyl, ethylsulfanyl, propylsulfanyl, isopropylsulfanyl, sec-butylsulfanyl and tert-butylsulfanyl; examples of $C_{1-4}$alkylsulfinyl include methylsulfinyl, ethylsulfinyl, propylsulfinyl, isopropylsulfinyl, sec-butylsulfinyl and tert-butylsulfinyl; examples of $C_{1-4}$alkylsulfonyl include methylsulfonyl, ethylsulfonyl, propylsulfonyl, isopropylsulfonyl, sec-butylsulfonyl and tert-butylsulfonyl; examples of $\underline{N}$—($C_{1-4}$alkyl)carbamoyl include $\underline{N}$-methylcarbamoyl and $\underline{N}$-ethylcarbamoyl; examples of $\underline{N},\underline{N}$-(di$C_{1-4}$alkyl)carbamoyl include $\underline{N},\underline{N}$-dimethylcarbamoyl and $\underline{N}$-methyl-$\underline{N}$-ethylcarbamoyl; examples of $C_{1-4}$alkanesulfenamido include methanesulfonamido, ethanesulphonamido and propanesulfonamido; examples of $C_{1-4}$alkanesulfonyl-N—$C_{1-4}$alkylamino include methylsulfonyl-N-methylamino, ethylsulfonyl-N-methylamino and propylsulfonyl-N-methylamino; examples of fluoro$C_{1-4}$alkyl include fluoromethyl, 2-fluoroethyl and 3-fluoropropyl; examples of difluoro$C_{1-4}$alkyl include difluoromethyl, 2,2-difluoroethyl and 3,3-difluoropropyl; examples of carbamoyl$C_{1-4}$alkyl include carbamoylmethyl, carbamoylethyl and carbamoylpropyl; examples of $\underline{N}$—($C_{1-4}$alkyl)carbamoyl$C_{1-4}$alkyl include $\underline{N}$-methyl-carbamoylmethyl and $\underline{N}$-ethyl-carbamoylethyl; examples of $\underline{N},\underline{N}$-(di$C_{1-4}$alkyl)carbamoyl-$C_{1-4}$allyl include $\underline{N},\underline{N}$-dimethylcarbamoylethyl and $\underline{N}$-methyl-$\underline{N}$-ethylcarbamoylethyl; examples of hydroxy$C_{1-4}$alkyl include hydroxymethyl, hydroxyethyl, hydroxypropyl, 2-hydroxypropyl, 2-(hydroxymethyl)propyl and hydroxybutyl; examples of $C_{1-4}$alkoxy$C_{1-4}$alkyl include methoxyethyl, ethoxyethyl and methoxybutyl; examples of sulfanyl$C_{1-4}$alkyl include sulfanylmethyl, sulfanylethyl, sulfanylpropyl; and examples of $\underline{N}$—($C_{1-4}$alkyl)amino$C_{1-4}$alkyl include N-methyl-aminomethyl and $\underline{N}$-ethyl-aminoethyl.

Examples of 5- or 6-membered heteroaryl ring systems include imidazole, triazole, pyrazine, pyrinmidine, pyridazine, pyridine, isoxazole, oxazole, isothiazole, thiazole and thiophene.

Preferably the NH group in imidazole is unsubstituted or substituted by $C_{1-4}$alkyl.

Examples of heterocyclyl rings include pyrrolidinyl, morpholinyl, piperidinyl, dihydropyridinyl and dihydropyrimidinyl.

Preferred heteroatoms are N and S, especially N. In general, attachment of heterocyclic rings to other groups is via carbon atoms.

Examples of values for $R^8$ in Formula (2) are side chains of lipophilic amino acids including such as for example methionine, phenylglycine, phenylalanine, serine, leucine, isoleucine or valine. L configuration in the corresponding free amino acid is preferred. Examples of amino acid side chains are set out below.

| Amino Acid | Side Chain |
| --- | --- |
| methionine | —$CH_2$—$CH_2$—S—$CH_3$ |
| phenylglycine | Ph |
| phenylalanine | —$CH_2$-Ph |
| thienylalanine | —$CH_2$-thien-2-yl |
| serine | —$CH_2OH$ or a $C_{1-4}$ alkyl (preferably methyl) ether thereof. |
| Leucine | —$CH_2$—$CHMe_2$ |
| homoserine | —$CH_2$—$CH_2$—OH or a $C_{1-4}$ alkyl (preferably methyl) ether thereof |
| $\underline{N}$-acetyl-lysine | —$CH_2$—$CH_2$—$CH_2$—$CH_2$—NH—CO—$CH_3$ |

The lactone in Formula (3) can be formed from a group of Formula (2) when $R^9$ is OH to give a carboxyl and $R^8$ is —$CH_2$—$CH_2$—OH where $R^8$ and $R^9$ together lose a water molecule to form part of a dihydrofuran-2-one heterocyclic ring.

Preferably $R^1$ is hydrogen, methyl or acetyl.
Most preferably $R^1$ is hydrogen.
Preferably $R^{12}$ and $R^{13}$ are independently hydrogen or methyl.
Most preferably $R^{12}$ and $R^{13}$ are hydrogen.
Preferably $Ar^1$ is of the formula (A) or (B).
Preferably $R^6$ is hydrogen, $C_{1-4}$alkyl, hydroxy$C_{1-4}$alkyl, amino$C_{1-4}$alkyl, fluoro$C_{1-4}$alkyl, difluoro$C_{1-4}$alkyl, $C_{1-4}$alkoxy or $C_{1-4}$alkoxy$C_{1-4}$alkyl.
More preferably $R^6$ is hydrogen, methyl, fluoromethyl, difluoromethyl, methoxy or methoxymethyl.
Most preferably $R^6$ is hydrogen or methyl.
Preferably m is 0 or 1.
Preferably $R^5$ is hydrogen or methyl.
More preferably $R^5$ is hydrogen.
Preferred heteroaryl value for $Ar^2$ are thiazolyl, pyridyl, triazolyl, pyrimidyl, pyrazinyl or pyridazinyl, especially thiazol-2-yl. When $Ar^2$ is phenyl, it is preferably unsubstituted or monosubstituted. In one aspect, when $Ar^2$ is phenyl, it is unsubstituted. In another aspect when $Ar^2$ is phenyl, it is monosubstituted in the para position.
Preferred substituents for ring carbon atoms in $Ar^2$ include $C_{1-4}$alkyl, halo, nitro, cyano and $C_{1-4}$alkoxy$C_{1-4}$alkyl.
More preferred substituents for ring carbon atoms in $Ar^2$ include methyl, ethyl, fluoro, chloro, cyano, methoxymethyl and ethoxyethyl.
When $Ar^2$ is phenyl it is preferably substituents by fluoro.
When $Ar^2$ is thiazolyl it is preferably unsubstituted.
Preferably $Ar^2$ is 4-fluorophenyl or thiazolyl.
Most preferably $Ar^2$ is 4-fluorophenyl or thiazol-2-yl.
In $Ar^3$, preferably at least three or W, X, Y and Z are CH.
Most preferably $Ar^3$ is phenyl.
Preferably n is 0 or 2.
In one aspect p is 0.
In another aspect p is 1.
$R^2$ is preferably a group of formula:

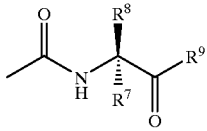

$R^7$ is preferably hydrogen or methyl, especially hydrogen.
In $R^8$, q is preferably 1–4, more preferably 1 or 2, especially 2.
Within $R^8$, $R^{10}$ is preferably $C_{1-4}$alkylsulfanyl, $C_{1-4}$alkylsulfinyl, $C_{1-4}$alkylsulfonyl, hydroxy or $C_{1-4}$alkoxy. More preferably $R^{10}$ is methylsulfanyl or methylsulfonyl.
$R^9$ is preferably hydroxy, $C_{1-4}$alkoxy, $C_{3-9}$cycloalkyloxy, heterocyclyloxy or heterocyclyl$C_{1-4}$alkoxy. More preferably $R^9$ is hydroxy, methoxy, propoxy, butoxy, tert-butoxy, cyclopentyloxy, piperidin-4-yloxy or morpholino$C_{1-4}$alkyl. Most preferably, $R^9$ is methoxy, propoxy, butoxy, tert-butoxy or cyclopentyloxy.
Preferably $R^{11}$ in $R^9$ is phenyl.
Preferred substituents for NH groups in heterocyclic groups in $R^9$ include methyl, ethyl, acetyl, propionyl, fluoromethyl, difluoromethyl and trifluoromethyl.
More preferred substituents for NH groups in heterocyclic groups in $R^9$ include methyl and acetyl.
Preferred substituents for ring carbon atoms in phenyl or heteroaryl groups in $R^{11}$ include methyl, halo, $C_{1-4}$alkanoyl, nitro, cyano, $C_{1-4}$alkylsulfinyl, $C_{1-4}$alkylsulfonyl, carbamoyl, $C_{1-4}$alkylcarbamoyl and di$C_{1-4}$alkylcarbamoyl.

Preferably $R^3$ is phenyl, pyridyl or thiazolyl.
Most preferably $R^3$ is phenyl.
Preferred substituents for ring carbon atoms in $R^3$ include $C_{1-4}$alkyl, halo, $C_{1-4}$alkoxy, nitro, cyano and $C_{1-4}$alkoxy$C_{1-4}$alkyl.
More preferred substituents for ring carbon atoms in $R^3$ include methyl, fluoro, chloro, methoxy, nitro, cyano and methoxymethyl.
A preferred substituent for a ring NH group in a heteroaryl group in $R^3$ is $C_{1-4}$alkyl, particularly methyl.
When $R^3$ is phenyl it is preferably substituted in the 4-position.
Preferably n is 0 or 2.
A preferred compound of the invention is a compound of the Formula (I) wherein:
$R^1$ is hydrogen, methyl or acetyl;
$Ar^1$ is of the formula (A) or (B);
$R^5$ is hydrogen or methyl;
$R^6$ is hydrogen, $C_{1-4}$alkyl, fluoro$C_{1-4}$alkyl, difluoro$C_{1-4}$alkyl, $C_{1-4}$alkoxy or $C_{1-4}$alkoxy$C_{1-4}$alkyl;
m is 0 or 1;
$R^{12}$ and $R^{13}$ are independently hydrogen or methyl;
$Ar^2$ is phenyl or thiazolyl;
$Ar^3$ is as hereinabove defined wherein at least three of W, X, Y and Z are CH; and
n is 0,1 or 2;
$R^2$ is of the formula (2) wherein $R^7$ is hydrogen or methyl;
$R^8$ is —$(CH_2)_q R^{10}$ wherein q is 0–4 and $R^{10}$ is $C_{1-4}$alkylsulfanyl, $C_{1-4}$alkylsulfinyl, $C_{1-4}$alkylsulfonyl, hydroxy or $C_{1-4}$alkoxy;
$R^9$ is hydroxy, $C_{1-4}$alkoxy, $C_{3-9}$cycloalkyloxy, heterocycloxy or heterocyclyl$C_{1-4}$alkoxy;
or $R^2$ is of the formula (3);
$R^3$ is phenyl, pyridyl or thiazolyl; and phenyl, heteroaryl and heterocyclyl rings in $R^3$, $R^9$ and $Ar^2$ are independently optionally substituted on ring carbon atoms by one or two substituents selected from $C_{1-4}$alkyl, halo, $C_{1-4}$alkoxy, $C_{1-4}$alkanoyl, nitro, cyano, $C_{1-4}$alkylsulfinyl, $C_{1-4}$alkylsulfonyl, carbamoyl, $C_{1-4}$alkylcarbamoyl and di$C_{1-4}$alkylcarbamoyl; and optionally substituted on ring NH groups by $C_{1-4}$alkyl, $C_{1-4}$alkanoyl, fluoromethyl, difluoromethyl or trifluoromethyl;
or a pharmaceutically-acceptable salt, prodrug or solvate thereof.
A more preferred compound of the invention is a compound of the formula (I) wherein:
$R^1$ is hydrogen, methyl or acetyl;
$Ar^1$ is of the formula (A) or (B);
$R^5$ is hydrogen or methyl;
$R^6$ is hydrogen methyl, fluoromethyl, difluoromethyl, methoxy or methoxymethyl;
m is 0 or 1;
$R^{12}$ and $R^{13}$ are independently hydrogen or methyl;
$Ar^2$ is phenyl or thiazolyl, optionally substituted on ring carbon atoms by one or two substituents selected from $C_{1-4}$alkyl, halo, nitro, cyano and $C_{1-4}$-alkoxy$C_{1-4}$alkyl;
$Ar^3$ as hereinabove defined wherein W, X, Y and Z are CH;
n is 0, 1 or 2;
$R^2$ is of formula (2) wherein $R^7$ is hydrogen or methyl;
$R^8$ is —$(CH_2)_q R^{10}$ wherein q is 1 or 2, and $R^{10}$ is methylsulfanyl or methylsulfonyl;

$R^9$ is hydroxy, methoxy, propoxy, butoxy, tert-butoxy, cyclopentyloxy, piperidin-4-yloxy, or morpholino$C_{1-4}$alkyl; or $R^2$ is of the formula (3);

$R^3$ is phenyl optionally substituted by one or two substituents selected from $C_{1-4}$alkyl, halo, $C_{1-4}$alkoxy, nitro, cyano and $C_{1-4}$alkoxy$C_{1-4}$alkyl; or a pharmaceutically-acceptable salt, prodrug or solvate thereof.

An even more preferred compound of the invention is a compound of the formula (I) wherein:

$R^1$ is hydrogen;

$Ar^1$ is of the formula (A) or (B);

$R^5$ is hydrogen or methyl;

$R^6$ is hydrogen or methyl;

m is 0 or 1;

$R^{11}$ and $R^{12}$ are hydrogen;

$Ar^2$ is phenyl or thiazol-2-yl wherein the phenyl ring is optionally substituted by fluoro;

$Ar^3$ is as hereinabove defined wherein W, X, Y and Z are CH;

n is 0, 1 or 2;

$R^2$ is of the formula (2) wherein $R^7$ is hydrogen;

$R^8$ is —$(CH_2)_qR^{10}$ wherein q is 2 and $R^{10}$ is methylsulfanyl or methylsulfonyl;

$R^9$ is hydroxy, methoxy, propoxy, butoxy, tert-butoxy, cyclopentyloxy, piperidin-4-yloxy, or 2-morpholinoprop2-yl;

$R^3$ is phenyl optionally substituted by fluoro;

or a pharmaceutically-acceptable salt, prodrug or solvate thereof.

Particular compounds of the present invention include:

(2S)-2-{2-(4-fluorophenyl)-4-[1-(4-fluorophenyl)-2-imidazol-1-yl)ethylamino]benzoylamino}-4-methylsulfanylbutyric acid;

methyl (2S)-2-{2-(4-fluorophenyl)-4-[1-(4-fluorophenyl)-2-(imidazol-1-yl)ethylamino]benzoylamino}-4-methylsulfanylbutyrate;

tert-butyl (2S)-2-{2-(4-fluorophenyl)-4-[1-(4-fluorophenyl)-2-(imidazol-1-yl)ethylamino]benzoylamino}-4-methylsulfanylbutyrate;

N-propanesulphonyl (2S)-2-{2-(4-fluorophenyl)-4-[1-(4-fluorophenyl)-2-(imidazol-1-yl)ethylamino]benzoylamino}-4-methylsulfanylbutyramide;

methyl (2S)-2-{2-phenyl-4-[1-(4-fluorophenyl)-2-(imidazol-1-yl)ethylamino]benzoylamino}-4-methylsulfanylbutyrate;

(2S)-2-{2-phenyl-4-[1-(4-fluorophenyl)-2-imidazol-1-yl)ethylamino]benzoylamino}-4-methylsulfanylbutyric acid;

methyl (2S)-2-{5-[1-(4-fluorophenyl)-2-imidazol-1-yl)ethylamino]-2-4-fluorophenethyl)benzoylamino}-4-methylsulfanylbutyrate;

(2S)-2-{5-[1-(4-fluorophenyl)-2-(imidazol-1-yl)ethylamino]-2-(4-fluorophenyethyl)benzoylaminoamino}-4-methylsulfanylbutyric acid;

methyl (2S)-2-{5[1-(4-fluorophenyl)-2-(imidazol-1-yl)ethylamino]-2-(4-fluorobenzyl)benzoylamino}-4-methylsulfanylbutyrate;

(2S)-2-{5-[1-(4-fluorophenyl)-2-(imidazol-1-yl)ethylamino]-2-(4-fluorobenzyl)benzoylamino}-4-methylsulfanylbutyric acid;

isopropyl (2S)-2-{5-[1-(4-fluorophenyl)-2-(imidazol-1-yl)ethylaminoethyl]-2-(4-fluorobenzyl)benzoylamino)}-4-methylsulfanylbutyrate;

(2S)-2-{5-[1-(4-fluorophenyl)-2-imidazol-1-yl)ethylaminomethyl]-2-(4-fluorobenzyl)benzoylamino}-4-methylsulfanylbutyric acid;

isopropyl (2S)-2-{5-[N-acetyl-1-(4-fluorophenyl)-2-(imidazol-1-yl)ethylaminomethyl]-2-4-fluorobenzyl)benzoylamino}-4-methylsulfanylbutyrate;

(2S)-2-{2-(4-fluorophenethyl)-5-[-1-(4-fluorophenyl)-2-(imidazol-1-yl)ethylaminomethyl]benzoylamino}-4-methylsulfanylbutyric acid;

isopropyl (2S)-2-{2-(4-fluorophenylethyl)-5-[1-(4-fluorophenyl)-2-(imidazol-1-yl)ethylaminomethyl]benzoylamino}-4-methylsulfanylbutyrate;

<u>N</u>-methylpiperidin-4-yl(2<u>S</u>)-2-{2-(4-fluorophenyl)-4-[1-(4-fluorophenyl)-2-imidazol-1-yl)ethylamino]benzoylamino}-4-methylsulfanylbutyrate;

tert-butyl (2S)-2-{2-(4-fluorophenyl)-4-[1-(4-fluorophenyl)-2-imidazol-1-yl)ethylamino]benzoylamino}-4-methylsulfonylbutyrate;

methyl (2S)-2-{2-(4-fluorophenyl)-4-[1-(4-fluorophenyl)-2-(imidazol-1-yl)ethylamino]benzoylamino}-4-methylsulfonylbutyrate;

(2S)-2-{2-(4-fluorophenyl)-4-[1-(4-fluorophenyl)-2-(imidazol-1-yl)ethylamino]benzoylamino}-4-methylsulfonylbutyric acid;

tert-butyl (2S)-2-{2-(phenyl)-4-[1-(4-fluorophenyl)-2-(imidazol-1-yl)ethylamino]benzoylamino}-4carbamoylbutyrate;

(2S)-2-{2-(phenyl)-4-[1-(4-fluorophenyl)-2-(imidazol-1-yl)ethylamino]benzoylamino}-4-carbamoylbutyric acid;

methyl (2S)-2-{2-(4-fluorobenzyl)-4-[1-(4-fluorophenyl)-2-(imidazol-1-yl)ethylamino]benzoylamino}-4-methylsulfanylbutyrate; and (2S)-2-{2-(4-fluorobenzyl)-4-[1-(4-fluorophenyl)-2-(imidazol-1-yl)ethylamino]benzoylamino}-4-methylsulfanylbutyric acid;

or a pharmaceutically-acceptable salt thereof.

In another aspect the present invention provides an inhibitor of ras farnesylation of Formula (1):

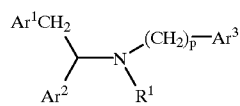

Formula (1)

wherein $Ar^1$ represents:

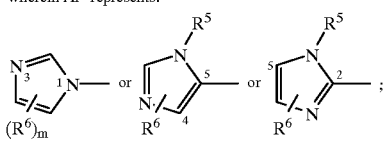

$Ar^2$ is phenyl or heteroaryl;

$R^1$ is hydrogen, $C_{1-4}$alkyl or $C_{1-4}$alkanoyl;

p is 0 or 1;

$Ar^3$ is of the formula:

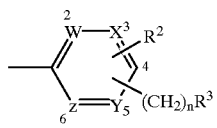

wherein W, X, Y and Z are independently is CH or N, provided that at least two of W, X, Y and Z are CH and $R^2$ and $-(CH_2)_nR^3$ are attached to ring carbon atoms; $R^2$ is a group of the Formula (2)

Formula (2)

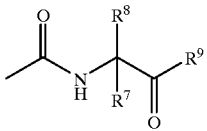

wherein $R^7$ is hydrogen or $C_{1-4}$alkyl, $R^8$ is $-(CH_2)_q-R^{10}$ wherein q is 0–4 and $R^{10}$ is $C_{1-4}$alkylsulfanyl, $C_{1-4}$alkylsulfinyl, $C_{1-4}$alkylsulfonyl, hydroxy, $C_{1-4}$alkoxy, carbamoyl, N—$C_{1-4}$alkylcarbamoyl, N,N-(di$C_{1-4}$allyl)carbamoyl, $C_{1-4}$alkyl, phenyl, thienyl, or $C_{1-4}$alkanoylamino, $R^9$ is hydroxy, $C_{1-4}$alkoxy, $C_{3-9}$cycloalkyloxy, heterocyclyloxy, heterocycyl$C_{1-4}$alkoxy or $-NH-SO_2R^{12}$ wherein $R^{12}$ represents trifluoromethyl, $C_{1-4}$alkyl, phenyl, heteroaryl, phenyl$C_{1-4}$alkyl or heteroaryl$C_{1-4}$alkyl; or $R^2$ represents a lactone of Formula (3)

Formula (3)

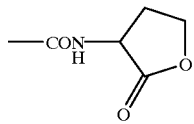

the group of Formula (2) or (3) having L or D configuration at the chiral alpha carbon in the corresponding free amino acid;

n is 0, 1 or 2;

$R^3$ is phenyl or heteroaryl;

$R^3$ and $Ar^2$ are independently optionally substituted by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, carbamoyl, N—$C_{1-4}$alkylcarbamoyl, N,N-(di-$C_{1-4}$alkyl)carbamoyl, $C_{1-4}$alkoxycarbonyl, thiol, $C_{1-4}$alkylsulfanyl, $C_{1-4}$alkylsulfinyl, $C_{1-4}$alkylsulfonyl, $C_{1-4}$alkanesulphonamido, N—($C_{1-4}$alkylsulfonyl)-N—$C_{1-4}$alkylamino, aminosulfonyl, N—($C_{1-4}$alkyl)aminosulfonyl, N,N-di ($C_{1-4}$alkyl) aminosulfonyl carbamoyl$_{C1-4}$alkyl, N—($C_{1-4}$alkyl) carbamoyl$C_{1-4}$alkyl, N,N-(di$C_{1-4}$alkyl)carbamoyl$C_{1-4}$alkyl, hydroxy$C_{1-4}$ alkyl and $C_{1-4}$alkoxy$C_{1-4}$alkyl;

$R^5$ is hydrogen, $C_{1-4}$alkyl, phenyl$C_{1-4}$alkyl;

$R^6$ is hydrogen, $C_{1-4}$alkyl, hydroxy$C_{1-4}$alkyl, sulfanyl$C_{1-4}$alkyl, N—($C_{1-4}$alkyl)amino$C_{1-4}$alkyl or phenyl$C_{1-4}$alkyl; m is 0,1 or 2;

provided that:

when n is 0, $Ar^3$ is substituted by $R^2$ in the 4-position and $-(CH_2)_nR^3$ in the 3- or 5-position and when n is 1 or 2, $Ar^3$ is substituted by $R^2$ in the 3- or 5-position and $-CH_2)_nR^3$ in the 4-position; position;

or a pharmaceutically acceptable salt, prodrug or solvate thereof.

In one aspect p is 0.

In another aspect p is 1.

Compounds of Formula (1) may form salts which are within the ambit of the invention. Pharmaceutically-acceptable salts are preferred although other salts may be useful in, for example, isolating or purifying compounds.

When the compound contains a basic moiety it may form pharmaceutically-acceptable salts with a variety of inorganic or organic acids, for example hydrochloric, hydrobromic, sulphuric, phosphoric, trifluoroacetic, citric or maleic acid. A suitable pharmaceutically-acceptable salt of the invention when the compound contains an acidic moiety is an alkali metal salt, for example a sodium or potassium salt, an alkaline earth metal salt, for example a calcium or magnesium salt, an ammonium salt or a salt with an organic base which affords a pharmaceutically-acceptable cation, for example a salt with methylamine, dimethylamine, trimethylamine, piperidine, morpholine or tris-(2-hydroxyethyl)amine.

Solvates, for example hydrates, are also within the ambit of the invention and may be prepared by generally known methods.

Various forms of prodrugs are well known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8 1–38 (1992);

d) H. Bundgaard, et al., Journal of Pharmaceutical Sciences, 77, 285 (1988); and e) N. Kakeya, et al., Chem Pharm Bull, 32, 692 (1984).

Examples of pro-drugs include in vivo hydrolysable esters of a compound of the Formula I. Suitable pharmaceutically-acceptable esters for carboxy include $C_{1-8}$alkyl esters, $C_{5-8}$cycloalkyl esters, cyclic amine esters, $C_{1-6}$alkoxymethyl esters for example methoxymethyl, $C_{1-6}$alkanoyloxymethyl esters for example pivaloyloxymethyl, phthalidyl esters, $C_{3-8}$-cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl wherein alkyl, cycloalkyl and cyclicamino groups are optionally substituted by, for example, phenyl, heterocyclcyl, alkyl, amino, alkylamino, dialkylamino, hydroxy, alkoxy, aryloxy or benzyloxy, and may be formed at any carboxy group in the compounds of this invention.

According to another aspect of the invention there is provided a pharmaceutical composition comprising a compound as defined in Formula (1) or an individual compound listed above together with a pharmaceutically-acceptable diluent or carrier. A preferred pharmaceutical composition is in the form of a tablet The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (1) will naturally vary according to the nature and severity of the conditions, the age and sex of the animal or patient and the route of administration, according to well known principles of medicine. As mentioned above, compounds of the Formula (1) are useful in treating diseases or medical conditions which are due alone or in part to the effects of farnesylation of ras.

In using a compound of the Formula (1) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

Compounds of this invention may be useful in combination with known anti-cancer and cytotoxic agents. If formulated as a fixed dose such combination products employ the compounds of this invention within the dosage range described herein and the other pharmaceutically active agent within its approved dosage range. Sequential use is contemplated when a combination formulation is inappropriate.

According to another aspect of the invention there is provided a compound of Formula (1) or a pharmaceutically-acceptable salt thereof, for use as a medicament.

According to another aspect of the invention there is provided a compound of Formula (1) or a pharmaceutically-acceptable salt thereof, for use in preparation of a medicament for treatment of a disease mediated through farnesylation of ras.

According to another aspect of the present invention there is provided a method of treating ras mediated diseases, especially cancer, by administering an effective amount of a compound of Formula (1) or a pharmaceutically-acceptable salt thereof, to a mammal in need of such treatment Diseases or medical conditions may be mediated alone or in part by farnesylated ras. A particular disease of interest is cancer. Specific cancers of interest include:

carcinoma, including that of the bladder, breast, colon, kidney, liver, lung, ovary, pancreas, stomach, cervix, thyroid and skin;

hematopoietic tumors of lymphoid lineage, including acute lymphocytic leukemia, B-cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, tetratocarcinoma, neuroblastoma and glioma.

The compounds of Formula (1) are especially useful in treatment of tumors having a high incidence of ras mutation, such as colon, lung, and pancreatic tumors. By the administration of a composition having one (or a combination) of the compounds of this invention, development of tumors in a mammalian host is reduced.

Compounds of Formula (1) may also be useful in the treatment of diseases other than cancer that may be associated with signal transduction pathways operating through Ras, e.g., neuro-fibromatosis.

Compounds of Formula (1) may also be useful in the treatment of diseases associated with CAAX-containing proteins other than Ras (e.g., nuclear lamins and transducin) that are also post-translationally modified by the enzyme farnesyl protein transferase.

Although the compounds of the Formula (1) are primarily of value as therapeutic agents for use in warm-blooded animals (including man), they are also useful whenever it is required to inhibit the effects of activation of ras by farnesylation. Thus, they are useful as pharmacological standards for use in the development of new biological tests and in the search for new pharmacological agents.

In another aspect the present invention provides a process for preparing a compound of the Formula (1) or a pharmaceutically-acceptable salt prodrug or solvate thereof which process comprises: deprotecting a compound of the formula (4)

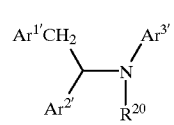

(4)

wherein $Ar^{1'}$ is $Ar^1$ or protected $Ar^1$, $Ar^{2'}$ is $Ar^2$ or protected $Ar^2$, $Ar^{3'}$ is $Ar^3$ or protected $Ar^3$ and $R^{20}$ is $R^1$ or an amino protecting group; wherein at least one protecting and thereafter if necessary:

(i) forming a pharmaceutically-acceptable salt, (ii) forming a prodrug, (iii) forming a solvate.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain $C_{1-12}$alkyl groups (for example isopropyl, t-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); phenyl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and t-butyldimethylsilyl); tri(lower alkyl)silyl lower alkyl groups (for example trimethylsilylethyl); and $C_{2-6}$alkenyl groups (for example allyl and vinylethyl).

Methods particularly appropriate for the removal of carboxy protecting groups include for example acid-, base-, metal- or enzymically-catalysed hydrolysis.

Examples of hydroxy protecting groups include lower alkyl groups (for example t-butyl), lower alkenyl groups (for example allyl); lower alkanoyl groups (for example acetyl); lower alkoxycarbonyl groups (for example t-butoxycarbonyl); lower alkenyloxycarbonyl groups (for example allyloxycarbonyl); phenyl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, t-butyldimethylsilyl) and phenyl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example t-butoxycarbonyl); lower alkenyloxycarbonyl (for example allyloxycarbonyl); phenyl lower alkoxycarbonyl groups (for example benzyloxycarbonyl, p-methoxybenzyloxycarbonyl, o-nitrobenzyloxycarbonyl, p-nitrobenzyloxycarbonyl; tri-alkylsilyl (for example trimethylsilyl and t-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl. photolytically.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

Compounds of the formula (1) and (4) can be formed by:
(i) reacting a compound of the formula (5) with a compound of the formula (6):

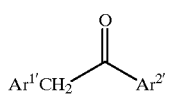

(5)

(6)

or (ii) converting one value of $R^9$ in $R^2$ into another value of $R^9$;

or (iii) reacting a compound in which $R^2$ in $Ar^{3'}$ is carboxy with a compound of the formula (7):

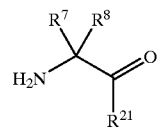

(7)

wherein $Ar^{1'}$, $Ar^{2'}$, $Ar^{3'}$, $R^7$–$R^{10}$ and $R^{20}$ are as hereinabove defined and $R^{21}$ is $R^9$ or a carboy protecting group; and thereafter if necessary:

(i) removing any protecting groups
(ii) forming a pharmaceutically-acceptable salt, prodrug or solvate thereof.

The compounds of the formula (5) and (6) are conveniently reacted together under conditions suitable for reductive amination, for example in the presence of a reducing agent and a dehydrating agent. Suitable reducing agents include sodium cyanoborohydride and sodium triacetoxyborohydride. When sodium cyanoborohydride is used, titanium tetrachloride or 3 Å or 4 Å molecular sieves may be used, in dichloromethane or an alcohol as solvent. When titanium tetrachloride is used, an organic base such as triethylamine is generally added. The reaction usually takes place in the temperature range of −20° C. to ambient temperature.

When p is 0 and sodium triacetoxyborohydride is used as the reducing agent, titanium tetrachloride is generally used as an activating agent, in an organic solvent such as dichloromethane, in a temperature range of −20° C. to ambient temperature. When p is 1 and sodium triacetoxyborohydride is used as the reducing agent, 4 Å molecular sieves are used as the dehydrating agent in an organic solvent such as dichloromethane, in a temperature range of −20° C. to ambient temperature. (Also see Synthesis 135, 1975; Org. Prep. Proceed. Int. 11 201, 1979).

A compound of the formula (5) can be prepared by introducing $Ar^{1'}$ into a compound of the formula (8):

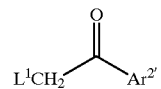

(8)

wherein $Ar^{2'}$ is as hereinabove defined and $L^1$ is a leaving group such as mesyloxy, tosyloxy, triflate or halo, preferably bromo. The reaction is conveniently carried out in the presence of a base such as sodium hydride, sodium hydroxide, butyl lithium or potassium carbonate. In some cases a base may not be necessary.

A compound of the formula (8) is conveniently formed from a compound of the formula (9):

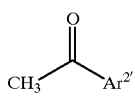

(9)

wherein $Ar^{2'}$ is as hereinabove defined.

The compound of the formula (9) may be converted to a compound in which $L^1$ is bromo by bromination with, for example, N-bromosuccinimide, carbon tetrabromide or bromine, or to a compound in which $L^1$ is chloro by chlorination with, for example, chlorine. When $L^1$ is mesyloxy or tosyloxy by oxidising the compound of the formula (9) to an alcohol and converting the hydroxy group to mesyloxy or tosyloxy with a mesyl halide or tosyl halide.

A compound of the formula (6) can be prepared by reducing the related nitro compound with a weak reducing agent such as ferric chloride in the presence of 1,1-dimethylhydrazine or tin chloride or hydrogenation under standard conditions known in the art.

The related nitro compound can be formed by introducing —$(CH_2)_nR^3$ into a compound of the formula (10):

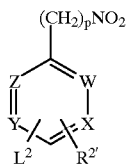

(10)

wherein $R^{2'}$, W, X, Y and Z are as hereinabove defined and $L^2$ is a leaving group.

When n is 0 and $R^3$ is phenyl, the compound of the formula (10) is conveniently reacted with phenyl boronic acid in the presence of a palladium catalyst such as palladium tetrakis(triarylphosphine)palladium (0) under conditions known for the Suzuki reaction (Synth. Commun. 11, 513 (1981)). An aprotic organic solvent such as dimethyl ether (DME), dimethylsulphoxide (DMSO) or THF is generally used and a base such as sodium bicarbonate, sodium carbonate and sometimes sodium hydroxide. A fluoride such as caesium fluoride could be used instead of the base (J. Org. Chem. 1994, 59, 6095–6097). Preferably $L^2$ is bromo or, when p is 1, triflate.

When n is 1 and $R^3$ is phenyl, the compound of the formula (10), wherein $L^2$ is preferably bromo or chloro, is conveniently reacted with a benzylzinc chloride or a benzylmagnesium bromide in the presence of a nickel or palladium catalyst, such as bis(triphenylphosphine)palladium (II) chloride or $Pd_2$(dibenzylideneacetone)$_3$, in an inert organic solvent such as tetrahydrofuran (THF). For example see the conditions used for the 'Nagishi' reaction (J. Org. Chem. 42 (10), 1821–1822, 1977).

When n is 2 and $R^3$ is phenyl, the compound of the formula (10) is conveniently reacted with a styrene under conditions known for the Heck reaction. Briefly this involves an inorganic or organic base such as triethylamine, a palladium catalyst such as bis (tri(o-tolyl)phosphine) palladium (II) chloride in water. (Acc. Chem. Res. 12, 146–151 (1979) or J. Organometallic Chem. 486,259–262 (1995)).

The resulting alkene can then be reduced using standard methods known in the art, for example, catalytic hydrogenation.

Alternatively the alkyne could be formed by reacting a compound of the formula (10) wherein $L^2$ is triflate or bromo with a phenyl acetylene in the presence of an organic base such as triethylamine and a palladium catalyst such as tetrakis (triphenylphosphine)palladium. For example see the conditions used for the Sonogashira reaction (J. Org. Chem. 1993,58, 6614–6619).

The resultant alkyne can be reduced using standard methods known in the art, for example, catalytic hydrogenation.

A compound of the formula (1) or (4) could be prepared via a sequence of steps from a compound of the formula (11):

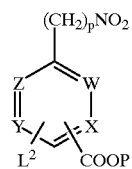

(11)

wherein p, $L^2$, W, X, Y and Z are as hereinabove defined and P is a carboxy protecting group.

$L^2$ can be replaced with the group —$(CH_2)_nR^3$ using the methodology described above. The nitro group could then be reduced to an amino group and the resultant compound reacted with a compound of the formula (5). The carboxy group in the resultant product can then be deprotected and reacted with the appropriate amino acid derivative to form $R^2$, and hence a compound of the formula (1) or (4), under conditions described hereinbelow.

Alternatively, when p is 1, a compound of the formula (6) could be prepared by reducing a compound containing a azidomethyl group in place of the aminomethyl group. The azido group could be formed from the corresponding bromomethyl group which in turn could be prepared from the corresponding hydroxymethyl compound.

A compound of the formula (1) in which $R^9$ is alkoxy can conveniently be hydrolysed to another compound of the formula (1) in which $R^9$ is hydroxy using standard methods known in the art. For example, the alkoxy group could be subjected to acid or base hydrolysis with, for example, in the case of base hydrolysis, aqueous sodium hydroxide solution in an organic solvent such as an alcohol in a temperature range of ambient temperature to 60° C.

When $R^9$ is a hydroxy group the carboxy group in a compound of the formula (1) can be converted to an acylsulphonamide by reacting the carboxy group with the appropriate sulphonamido group in the presence of an organic base such as triethylamine or dimethylaminopyridine, in an inert organic solvent such as dimethylformamide (DMF), in temperature range of −20° C. to ambient temperature.

The reaction between a compound in which $R^2$ in $Ar^{3'}$ is carboxy and a compound of the formula (7) is generally carried out in the presence of a reagent that converts the carboxy group into a reactive ester, for example a carbodiimide such as 1-(3-dimethylaminopropyl)-3-ethylcarbodiimide (EDC) or pentafluorophenyl, and in the presence of an organic base such as N-methylmorpholine or dimethylaminopyridine (DMAP). The reaction is usually carried out in the temperature range of −20° C. to ambient temperature. The reagent, 1-hydroxybenzotriazole, is often added to assist the reaction (see Chem. Ber. 103, 788, 2024 (1970), J. Am. Chem. Soc. 93, 6318 (1971), Helv. Chim. Acta. 56, 717, (1973)). Suitable solvents include DMF and dichloromethane.

A compound of the formula (1) in which $R^2$ in $Ar^{3'}$ is carboxy can be prepared by reacting a compound of the formula (5) with a compound of the formula (6) wherein $R^2$ in $Ar^{3'}$ is protected carboxy and subsequently removing the protecting group.

Optionally substituents in a compound of the formula (1) and (4) or intermediates in their preparation may be converted into other optional substituents. For example an alkylthio group may be oxidised to an alkylsulphinyl or alkysulphonyl group, a nitro group reduced to an amino group, a hydroxy group alkylated to a methoxy group, or a bromo group converted to an alkylthio group.

Various substituents may be introduced into compounds of the formulae (1) and (4) and intermediates in this preparation, when appropriate, using standard methods known in the art. For example, an acyl group or alkyl group may be introduced into an activated benzene ring using Friedel-Crafts reactions, a formyl group by formylation with titanium tetrachloride and dichloromethyl ethyl ester, a nitro group by nitration with concentrated nitric acid concentrated sulphuric acid and bromination with bromine or tetra(n-butyl)ammonium tribromide.

It will be appreciated that, in certain steps in the reaction sequence to compounds of the formula (1), it will be necessary to protect certain functional groups in intermediates in order to prevent side reactions. Deprotection may be carried out at a convenient stage in the reaction sequence once protection is no longer required.

Biological activity was tested as follows:

(i) In-vitro assay

The following stock solutions were used and the assays were conducted in 96 well plates: TRIS Buffer (500 mM TRIS, 50 mM $MgCl_2.6H_2O$, pH=8.0); Farnesyl pyrophosphate (6.4 mg/ml); Aprotinin (1.9 mg/ml); Ki-ras (0.5 mg/ml, stored at −80° C.); Acid ethanol (850 ml absolute ethanol+150 ml concentrated HCl).

Farnesyl protein transferase (FPT) was partially purified from human placenta by ammonium sulphate fractionation followed by a single Q-Sepharose™ (Pharmacia, Inc) anion exchange chromatography essentially as described by Ray and Lopez-Belmonte (Ray K P and Lopez-Belmonte J (1992) Biochemical Society Transactions 20 494–497). The substrate for FPT was Kras (CVIM C-terminal sequence). The cDNA for oncogenic val12 variant of human c-Ki-ras-2 4B was obtained from the plasmid pSW11-1 (ATCC). This was then subcloned into the polylinker of a suitable expression vector e.g. pIC147. The Kras was obtained after expression in the E. coli strain, BL21. The expression and purification of c-KI-ras-2 4B and the val12 variant in E. coli has also been reported by Lowe et al (Lowe P N et al. J. Biol. Chem. (1991) 266 1672–1678). The farnesyl protein transferase enzyme preparation was stored at −80° C.

The farnesyl transferase solution for the assay contained the following: dithiothreitol (DTT)(0.6 ml of 7.7 mg/ml), TRIS buffer (0.6 ml), aprotinin (0.48 ml), distilled water (1.2 ml), farnesyl transferase (0.6 ml of the crude enzyme preparation prepared as described above), zinc chloride (12 μl of 5 mM). This was left at room temperature for 30 minutes. After this incubation 60 μl Ki-ras solution was added and the whole left to incubate for a further 60 minutes prior to use in the assay.

Assays were performed in 96 well plates as follows: 10 μl of test compound solution was added to each well. Then 30 μl farnesyl transferase solution (above) was added and the reaction started by addition of 10 μl radiolabelled farnesyl pyrophosphate solution. After 20 minutes at 37° C. the reaction was stopped with 100 μl acid ethanol (as described in Pompliano D L et al (1992) 31 3800–3807). The plate was then kept for 1 hour at 4° C. Precipitated protein was then collected onto glass fibre filter mats (B) using a Tomtec™ cell harvester and tritiated label was measured in a Wallac™1204 Betaplate scintillation counter. Test compounds were added at appropriate concentrations in DMSO (3% final concentration in test and vehicle control).

(ii) Intracellular Farnesylation Assay

HER313A cells (Grand et al, 1987 Oncogene 3, 305–314) were routinely cultured in Dulbecos Modified Essential Medium (DMEM) plus 10% foetal calf serum (FCS). For the assay HER313A cells were seeded at 200,000 cells/well in a volume of 2.5 ml in a 6 well tissue culture plate. After an overnight incubation at 37° C. in 10% $CO_2$ the medium was removed and replaced with methionine-free minimal essential medium (MEM) and the cells incubated as above for 2 hours. After this time the medium was removed and replaced by methionine-free MEM (1 ml) and test compound (1–3 μl). The plates were then incubated for a further 2 hours as described above and then 30 μCi of $^{35}S$-methionine added to each well. The plate was then incubated overnight as described above. The medium was then removed and the cells were lysed with lysis buffer (1 ml) (composed of 1000 ml phosphate buffered saline, 10 ml trition X-100, 5 g sodium deoxycholate, 1 g sodium dodecylsulphate) containing aprotinin (10 μl/ml), the plate scrapped and then left for 10 minutes at 4° C. The lysate was then clarified by centrifugation. To 0.8 ml of the clarified lysate 80 μl of Y13-259 pan-Ras antibody (isolated from the hybridoma—American Tissue Culture Collection Accession Number CRL-1742) (final concentration approximately 1 μg/ml, the exact working concentration was optimised for each batch of antibody isolated) and protein G beads (30 μl of 0.5 μg/ml) were added and the mixture incubated overnight with constant agitation. The pellet was then collected by centrifugation, washed and separated by SDS PAGE using a 15% gel. Radioactive bands were detected using a phosphorimager system.

(iii) Morphology and proliferation assay

MIA PaCa 2 cells (American Tissue Culture Collection Accession Number: CRL-1420) were routinely cultured in Dulbecos Modified Essential Medium (DMEM) plus 10% FCS in a 162 $cm^2$ tissue culture flask. For the assay the cells were seeded at 16,000 cells/well, in 12 well plates, in DMEM containing 5% charcoal dextran treated stripped FCS (1 ml)(obtained from Pierce and Warriner). The cells were then incubated overnight at 37° C. in 10% $CO_2$. Test compound was then added (10 μl) and the cells incubated for 6 days as described above. On days 1, 2, 3 and 6 the cells were monitored for signs of morphological change and toxicity. On day 6 the cells were removed from the plate using trypsin/EDTA and counted to determine the proliferation rate.

Although the pharmacological properties of the compounds of the Formula (1) vary with structural change as expected, in general compounds of the Formula (1) possess an $IC_{50}$ in the above test in the range, for example, 0.0005 to 50 μM. Thus by way of example the compound of Example 6 herein has an $IC_{50}$ of approximately 0.002 μM. No physiologically unacceptable toxicity was observed at the effective dose for compounds tested of the present invention.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) C18 reverse phase silica separation;

(iv) yields are given for illustration only and are not necessarily the maximum attainable;

(v) the end-products of the Formula (1) have satisfactory microanalyses and their structures were confirmed by nuclear magnetic resonance (NMR) and mass spectral techniques; chemical shift values were measured on the delta scale; the following abbreviations have been used: s, singlet; d, doublet; t or tr, triplet; m, multiplet; br, broad;

(vi) intermediates were not generally fully characterised and purity was assessed by thin layer chromatographic, HPLC, infra-red (IR) or NMR analysis;

(vii) melting points are uncorrected and were determined using a Mettler SP62 automatic melting point apparatus or an oil-bath apparatus; melting points for the end-products of the Formula (1) were determined after crystallisation from a conventional organic solvent such as ethanol, methanol, acetone, ether or hexane, alone or in admixture; and (viii) the following abbreviations have been used:

DMA N,N-dimethylacetamide

DMAP 4-dimethyl-aminopyridine

DMF N,N-dimethylformamide

DMSO dimethylsulfoxide

EDC 1-(3-dimethylaminopropyl)-3-ethyl carbodiimide

HOBT 1-hydroxybenzotriazole

MCPA M-chloroperoxybenzoic acid

TFA trifluoroacetic acid

THF tetrahydrofuran

EXAMPLE 1

(2S)-2-{2-(4-Fluorophenyl)-4-[1-(4-fluorophenyl)-2-(imidazol-1-yl)ethylamino]benzoylamino}-4-methylsulfanylbutyric acid A solution of methyl (2S)-2-{2-(4-fluorophenyl)-4-[1-(4-fluorophenyl)-2-(imidazol-1-yl)ethylamino]benzoylamino}-4-methylsulfanylbutyric (0.15 g; 0.26 mmol) in methanol (5 ml) was treated with 2N aqueous sodium hydroxide solution (0.5 ml) and stirred at ambient temperature for 1 hour. After evaporation of the methanol, the aqueous reaction mixture was acidified to pH 7.5 with 6N HCl and purified on reverse phase silica eluting with a gradient of 50–60% methanol/ammonium carbonate buffer (2 g/l, pH 7). The appropriate fractions were concentrated and freeze-dried to give the title compound as a solid.

Yield: 84%

$^1$H NMR (DMSO d$_6$+CF$_3$COOD, 400 MHz) δ: 1.7–1.95 (2H, m); 2 (3H, s); 2.15–2.35 (2H, m); 4.20 (1H, m); 4.52 (2H, m); 5.17 (1H, m); 6.5–6.65 (2H, m); 7.05–7.35 (7H, m); 7.5 (2H, m); 7.65 (1H, s); 7.8 (1H, m); 9.06 (1H, s).

Anal. Calculated for C$_{29}$H$_{28}$F$_2$N$_4$O$_3$S, 1.6 H$_2$O

| | | | | |
|---|---|---|---|---|
| C 60.30 | H 5.41 | N 9.16 | S 5.20 | |
| Found | C 60.57 | H 5.19 | N 9.25 | S 5.21 |

MS (ESI) m/z 511 (MH$^+$)

The starting material was prepared as follows:

4-Fluorophenylboronic acid (6.72 g; 0.048 mol) was added to a suspension of 2-bromo-4-nitrotoluene (6.9 g; 0.032 mol) and tetrakis(triphenylphosphine) palladium (1.5 g; 1.4 mmol) in DME (90 ml). After addition of aqueous sodium carbonate solution 2M (120 ml), the mixture was refluxed overnight. After extraction with ether and evaporation, the residue was purified by flash chromatography (ethyl acetate/petroleum ether 95/5 to give 2-(4-fluorophenyl)-4-nitrotoluene (6.66 g; 90%).

$^1$H NMR (CDCl$_3$, 400 MHz) δ: 2.34 (3H, s); 7.1–7.5 (5H, m); 8.10 (2H, m).

Potassium permanganate (23 g; 0.145 mol) was added to a solution of 2-(4-fluorophenyl)-4-nitrotoluene (6.46 g; 0.028 mol) in pyridine/water (100 ml/60 ml). The solution was heated to reflux with care. After reflux overnight, the insoluble material was filtered off and the mixture evaporated to dryness. The residue was taken up in a 2N aqueous sodium hydroxide solution, washed with ether and acidified with 12N HCl. The mixture was extracted with ether, the organic layer was evaporated to dryness to give 2-(4-fluorophenyl)-4-nitrobenzoic acid (5.76 g; 79%).

$^1$H NMR (CDCl$_3$+CF$_3$COOD, 400 MHz) δ: 7.1–7.3 (4H, m); 8.1–8.35 (2H, m).

Oxalyl chloride (9.35 g; 0.074 mol) was added to a solution of 2-(4-fluorophenyl)-4-nitrobenzoic acid (17.5 g; 0.067 mol) in methylene chloride (150 ml). After addition of DMF (3 drops), the mixture was stirred at ambient temperature for 2 hours. After evaporation to dryness the residue was redissolved in methylene chloride (100 ml); methanol (50 ml) and DMAP (8.2 g; 0.067 mol) was added at 0° C. After stirring at ambient temperature for 2 hours, the mixture was evaporated to dryness. The residue was taken up in methylene chloride washed with a 2N HCl, saturated aqueous sodium bicarbonate and evaporated to give methyl 2-(4-fluorophenyl)-4-nitrobenzoate (17.6 g; 95%).

$^1$H NMR (CDCl$_3$, 400 MHz) δ: 3.71 (3H, s); 7.05–7.4 (4H, m); 7.9 (1H, m); 8.26 (2H, m).

A solution of methyl-2-(4-fluorophenyl)-4-nitrobenzoate (17 g; 0.062 mol) in methylene chloride (60 ml) and methanol (400 ml) was hydrogenated on 10% Pd/C (2 g). After filtration of the catalyst, the mixture was evaporated and purified by flash chromatography eluting with methanol/methylene chloride 10/90 to give after evaporation methyl 4-amino-2-(4-fluorophenyl)benzoate (15 g; 100%).

$^1$H NMR (CDCl$_3$, 400 MHz) δ: 3.65 (3H, s); 4.05 (2H, s); 6.5 (1H, m); 6.65 (1H, m); 7–7.3 (4H, m); 7.84 (1H, d).

Titanium chloride (2.86 ml; 26 mmol) was added portionwise to a solution of methyl 4-amino-2-(4-fluorophenyl) benzoate (5 g; 20 mmol), 1-(4-fluorophenyl)-2-(imidazol-1-yl) ethanone (4.08 g; 20 mmol) and triethylamine (8.4 ml; 60 mmol) in dichloromethane (120 ml) at 0° C. under argon atmosphere. After stirring overnight at ambient temperature, sodium cyanoborohydride (1.4 g; 0.22 mmol) in solution in methanol (10 ml) was added at 0° C. The reaction mixture was stirred for 2 hours at ambient temperature, treated with 5% aqueous sodium hydrogen carbonate solution, filtered and extracted with dichloromethane. After evaporation to dryness of the organic phase, the residue was purified by flash chromatography eluting with dichloromethane/ethanol 95/5 to give methyl 4-[1-(4-fluorophenyl)-2-(imidazol-1-yl) ethylamino]-2-(4-fluorophenyl)benzoate. Yield 52%.

$^1$H NMR (CDCl$_3$, 400 MHz) δ: 3.51 (3H, s); 4.22 (2H, m); 4.40 and 4.70 (1H, m); 6.30 (1H, m); 6.37 (1H, m); 6.68 (1H, s); 6.9–7.25 (10H, m); 7.68 (1H, d).

MS (ESI) m/z 434 (MH$^+$)

Methyl 4-[1-(4-fluorophenyl)-2-(imidazol-1-yl) ethylamino]-2-(4-fluorophenyl)benzoate (4.36 g; 10 mmol) in methanol (100 ml) was treated with 2N aqueous sodium hydroxide solution (20 ml; 40 mmol) at reflux for 24 hours. After evaporation of the methanol, the residue was taken up in water, the pH adjusted to 4.5 with HCl 2N. The resulting precipitate was filtered, washed with water and pentane to give 4-[-(4-fluorophenyl)-2-(imidazol-1-yl)ethylamino]-2-(4-fluorophenyl)benzoic acid as a solid (4 g; 95%).

M.P.: 195–200° C.

$^1$H NMR (DMSO d$_6$+CF$_3$COOD, 400 MHz) δ: 4.52 (2H, m); 5.17 (1H, m); 6.45 (1H, s); 6.56 (1H, m); 7–7.3 (6H, m); 7.4–7.7 (4H, m); 7.80 (1H, s); 9.08 (1H, s).

MS (ESI) m/z 420 (MH$^+$)

EXAMPLE 2

Methyl (2S)-2-{2-(4-fluorophenyl)-4-[1-(4-fluorophenyl)-2-(imidazol-1-yl)ethylamino]benzoylamino}-4methylsulfanylbutyrate A mixture of 4-{1-(4-fluorophenyl)-2-(imidazol-1-yl) ethylamino]-2-(4-fluorophenyl)benzoic acid (1.67 g; 4 mmol), methyl (2S)-2-amino-4-(methylsulfanyl)butanoate, (L-methionine methyl ester hydrochloride) (0.96 g; 4.8 mmol), HOBT (0.65 g; 4.8 mmol), EDC (0.925 g; 4.8 mmol) and DMAP (0.54 g; 4.4 mmol) in dichloromethane (100 ml) was stirred at ambient temperature for 5 hours. The solution was diluted with dichloromethane (200 ml), washed with 5% aqueous sodium hydrogen carbonate solution and evaporated to dryness. The residue was purified by flash chromatography eluting with dichloromethane/ethanol 95/5 to give the title compound as a solid (1.8 g; 80%).

M.P.: 94–98° C.

$^1$H NMR (CDCl$_3$, 400 MHz) 67 : 1.5–2.1 (2H, m); 2.01 (3H, s); 2.1–2.25 (2H, m); 3.64 (3H, s); 4.2–4.8 (5H, m); 5.77 (1H, m); 6.37 (1H, m); 6.48 (1H, m); 6.76 (1H, m); 6.95–7.35 (10H, m) 7.52 (1H, m).

Anal. Calculated for C$_{30}$H$_{30}$F$_2$N$_4$O$_3$S, 0.6 H$_2$O

| C 62.52 | H 5.46 | N 9.74 | S 5.57 | |
|---|---|---|---|---|
| Found | C 62.86 | H 5.68 | N 9.86 | S 5.35 |

EXAMPLE 3

Tert-butyl (2S)-2-{2-(4-fluorophenyl)-4-[1-(4-fluorophenyl-2-(imidazol-1-yl)ethylamino]benzoylamino}-4-methylsulfanylbutyrate The title compound was prepared using a similar method to that described for methyl (2S)-2-{2-(4-fluorophenyl)-4-{1-(4-fluorophenyl)-2-(imidazol-1-yl)ethylamino] benzoylamino}-4-methylsulfanylbutyrate, but using tert-butyl (2S)-2-amino-4-(methylsulfanyl)butanoate (L-methionine tert-butyl ester) in place of the L-methionine methyl ester.

Yield: 80%

M.P.: 104–106° C.

$^1$H NMR (CHCl$_3$, 400 MHz) δ: 1.4 (9H, s); 1.7–2 (2H, m); 2.02 (3H, s); 2.1–2.25 (2H, m) 4.2–4.4(3H, m); 4.48(1H, m); 4.75 (1H, m); 5.80 (1H, m); 6.38 (1H, m); 6.48 (1H, m); 6.76 (1H, s); 7–7.3 (5H, m); 7.48 (1H, d).

Anal. Calculated for C$_{33}$H$_{36}$F$_2$N$_4$O$_3$S, 0.5 H$_2$O

| C 64.37 | H 6.06 | N 9.10 | S 5.21 | |
|---|---|---|---|---|
| Found | C 64.42 | H 5.98 | N 8.41 | S 4.67 |

MS (ESI) m/z 607 (MH$^+$)

EXAMPLE 4

N-Propanesulphonyl (2S)-2-{2-(4-fluorophenyl)-4-[1-(4-fluorophenyl)-2-imidazol-1-yl)ethylamino]benzoylamino}-4-methylsulfanylbutyramide The title compound was prepared using a similar method to that of Example 2, but using N-propanesulphonyl (2S)-4-methylsulfanylbutyramide in place of L-methionine methyl ester.

Yield: 51%

M.P.: 140–143° C.

$^1$H NMR (DMSO d$_6$, 400 MHz) δ: 0.9 (3H, m); 1.75 (2H, m); 1.80–1.90 (2H, m); 2.01 (3H, s); 2.15–2.35 (2H, m); 3.15–3.25 (2H, m); 4.1–4.35 (3H, m); 5.0 (1H, m); 6.52 (2H, m); 6.8–6.9 (2H, m); 7.1–7.3 (8H, m); 7.46 (2H, m); 7.68 (1H, s); 8.06 (1H, m).

Anal. Calculated for C$_{32}$H$_{35}$N$_5$O$_4$S$_2$F$_2$, 0.6 H$_2$O

| C 57.66 | H 5.47 | N 10.51 | S 9.62 | |
|---|---|---|---|---|
| Found | C 57.48 | H 5.48 | N 10.70 | S 9.06 |

MS (ESI) m/z 656 (MH$^+$)

EXAMPLE 5

Methyl (2S)-2-{2-Phenyl-4-[1-(4-fluorophenyl)-2-(imidazol-1-yl)ethylamino]benzoylamino}-4-methylsulfanylbutyrate The title compound was prepared using a similar method to that of Example 2, but using methyl 4-amino-2-phenylbenzoate in place of methyl 2-(4-fluorophenyl)-4-aminobenzoate.

Yield: 30%

$^1$H NMR (CDCl$_3$, 400 MHz) 67 : 1.5–1.95 (2H, m); 2 (3H, m); 2.05–2.15 (2H, m); 3.02 (3H, s); 4.3 (3H, m); 4.6 (1H, m); 4.77 (1H, m); 5.65 (1H, m); 6.3–6.55 (2H, m); 6.75 (1H, s); 7–7.65 (12H, m).

Anal. Calculated for $C_{30}H_{31}FN_4O_3S$, 0.2 $H_2O$

| | | | |
|---|---|---|---|
| C 65.48 | H 5.75 | N 10.18 | S 5.83 |
| Found C 65.36 | H 5.85 | N 10.26 | S 5.40 |

MS (ESI) m/z 546 (MH$^+$)

EXAMPLE 6

(2S)-2-{2-Phenyl-4-[1-(4-fluorophenyl-2-imidazol-1-yl)ethylamino]benzoylamino}-4-methylsulfanylbutyric acid The title compound was prepared using a similar method to that of Example 1.

Yield: 87%

$^1$H NMR (DMSO d$_6$+CF$_3$COOD, 400 MHz) δ: 1.7–1.95 (2H, m); 2 (3H, s); 2.1–2.35 (2H, m); 4.22 (1H, m); 4.5 (2H, m); 5.1 (1H,m); 6.57 (2H, m); 7.1–7.35 (8H, m); 7.5 (2H, m); 7.66 (1H, s); 7.8 (1H, m); 9.06 (1H, s).

Anal. Calculated for $C_{29}H_{29}FN_4O_3S$, $H_2O$

| | | | |
|---|---|---|---|
| C 63.19 | H 5.68 | N 10.16 | S 5.82 |
| Found C 62.91 | H 5.39 | N 10.0 | S 5.58 |

EXAMPLE 7

Methyl (2S)-2-{5-1-(4-fluorophenyl)-2-(imidazol-1-yl)ethylamino]-2-(4-fluorophenethyl)benzoylamino}-4-methylsulfanylbutyrate The title compound was prepared using a similar method to that of Example 2, but using methyl 5-amino-2-(4-fluorophenethyl)benzoate in place of methyl 4-amino-2-(4-fluorophenyl)benzoate.

Yield: 84%

M.P.: 120–125° C.

$^1$H NMR (DMSO d$_6$+CF$_3$COOD, 400 MHz) δ: 1.95–2.15 (2H, m); 2.06 (3H, s); 2.4–2.6 (2H, m); 2.65–2.9 (4H, m); 3.77 (3H, s); 4.45–4.6 (3H, m); 5.05 (1H, m), 6.5 (1H, d); 6.62 (1H, m); 6.88 (1H, m); 7.00–7.25 (6H, m); 7.52 (2H, m); 7.65 (1H, m); 7.85 (1H, s); 9.14 (1H, s).

Anal. Calculated for $C_{32}H_{34}F_2N_4O_3S$, 1 $H_2O$, 1.5 HCl

| | | | |
|---|---|---|---|
| C 57.76 | H 5.68 | N 8.42 | S 4.82 |
| Found C 57.90 | H 5.74 | N 8.67 | S 4.84 |

MS (ESI) nm/z 593 (MH$^+$)

Methyl 5-amino-2-(4-fluorophenylethyl)benzoate was prepared as follows:

A mixture of methyl 2-bromo-5-nitrobenzoate (5 g), 4-fluorostyrene (3.5 g), tributylamine (0.39 g), bis-(triphenylphosphine)-palladium(II)chloride (0.3 g), sodium bicarbonate(2.65 g) and water (30 ml) was stirred and heated at reflux under an argon atmosphere for 1.5 hours. The reaction was then cooled, suspended in dichloromethane (200 ml) and passed through a pad of silica (chromatography grade) eluting with more dichloromethane The dichloromethane was then evaporated away and the residue treated with iso-hexane (200 ml) to give as a yellow precipitate which was filtered and dried, (5.05 g).

NMR (CDCl$_3$) 67 : 3.99(s, 3H), 7.08(t, 2H), 7.15(d, 1H), 7.55(q, 2H), 7.88(d, 1H), 8,0(d, 1H), 8.32(2d, 1H), 8.8(d, 1H).

A mixture of methyl 2-[2-(4-fluorophenyl)ethynyl]-5-nitrobenzoate (29 g), 10% Pd/C (3 g), and ethyl acetate (400 ml)was stirred under an hydrogen atmosphere for 6 hours. The catalyst was removed by filtration and replaced by fresh catalyst (3 g). The hydrogenation was then continued for another 16 hours, the catalyst was again filtered off, the filtrate evaporated to dryness and the residue treated with iso-hexane to give a white precipitate which was isolated by filtration and dried to give methyl 5-amino-2-4-fluorophenethyl)benzoate (23.5 g).

NMR (CDCl$_3$) 67 : 2.8(t, 2H), 3.1 (t, 2H), 3.62(s, 2H), 3.88(s, 3H), 6.72(dd, 1H), 6.93 (m, 3H), 7.13(m, 2H), 7.23(d, 1H).

EXAMPLE 8

(2S)-2-{5-[1-(4-Fluorophenyl)-2-(imidazol-1-yl)ethylamino]-2-(4-fluorophenethyl)benzoylamino}-4-methylsulfanylbutyric acid The title compound was prepared using a similar method to that of Example 1.

Yield: 63%

M.P.: 115–120° C.

$^1$H NMR (DMSO d$_6$+CF$_3$COOD, 400 MHz) 67 : 1.9–2.2 (2H, m); 2.03 (3H, s); 2.45–2.65 (2H, m); 2.60–2.80 (4H, m); 4.49 (3H, m); 5.01 (1H, m); 6.46 (1H, m); 6.62 (1H, m); 6.88 (1H, d); 7.03 (1H, m); 7.15–7.25 (4H, m); 7.50 (2H, m); 7.65 (1H, d); 7.82 (1H, d); 9.06 (1H, s).

Anal. Calculated for $C_{31}H_{32}F_2N_4O_3S$, 1.4 $H_2O$

| | | | |
|---|---|---|---|
| C 61.66 | H 5.81 | N 9.28 | S 5.31 |
| Found C 62.02 | H 5.66 | N 9.44 | S 4.93 |

MS (ESI) m/z 579 (MH$^+$)

EXAMPLE 9

Methyl (2S)-2-{5-[1-(4- fluorophenyl)-2-(imidazol-1-yl)ethylamino]-2-(4-fluorobenzyl)benzoylamino}-4-methylsulfanylbutyrate The title compound was prepared using a similar method to that of Example 2, but using methyl 5-amino-2-(4-fluorobenzyl)benzoate in place of methyl 2-(4-fluorophenyl)-4-aminobenzoate.

Yield: 88%

$^1$H NMR (DMSO d$_6$+CF$_3$COOD, 400 MHz) δ: 1.9–2.1 (2H, m); 2 (3H, s); 2.35–2.60 (2H, m); 3.65 (3H, s,); 3.7.–4 (2H, m); 4.5 (3H, m); 5 (1H,m); 6.45–7.2 (9H, m); 7.4 (4H,m); 9.14 (1H, s).

Anal. Calculated for $C_{31}H_{32}F_2N_4O_3S$ 1.3 $H_2O$, 1.7HCl

| | | | |
|---|---|---|---|
| C 56.07 | H 5.51 | N 844 | S 4.83 |
| Found C 56.09 | H 5.58 | N 8.49 | S 5.11 |

MS (ESI) m/z 579 (MH$^+$)

Methyl 5-amino-2-(4-fluorobenzyl)benzoate was prepared as follows:

Zinc dust (14.2 g, 217.2 mmol) and tetrahydrofuran (17 ml) were sonicated under argon for 30 minutes. Dibromoethane (2.1 ml, 24.38 mmol) was added and the mixture heated to 67° C. for 1 minute, cooled to 25° C. and trimethylsilyl chloride (2.5 ml, 19.58 mmol) added. After initial effervescence and exotherm, the mixture was stirred at ambient temperature for 30 minutes. 3M 4-Fluorobenzyl bromide (26 ml, 212 mmol) in tetrahydrofuran (70 ml) was added dropwise with exotherm and stirred at ambient temperature for 1.5 hours. To this a solution of tris (dibenzylideneacetone)palladium(0) (1.3 g, 1.42 mmol) and methyl 2-bromo-5-nitrobenzoate (44 g, 170 mmol) in tetrahydrofuran (550 ml) was added dropwise, under argon, over 30 minutes with exotherm and stirred at ambient for 18 hours. The mixture purified on silica (eluting with ethyl acetate), washed with brine (200 ml) and water (200 ml), dried (magnesium sulphate) and evaporated to give methyl 3-nitro-6-(4-fluorobenzyl)benzoate (65 g) which was used in the next step without further purification.

$^1$H NMR (CDCl3, 300 MHz) δ3.92(3H,s); 4.44(2H, s); 6.93–7.00(2H, t); 7.07–7.13(2H, m); 7.35–7.39(1H, d); 8.24–8.26(1H, d); 8.76(1H, s).

A solution of methyl 3-nitro-6-(4-fluorobenzyl)benzoate (10 g, 36.9 mmol) in ethyl acetate (740 ml) was treated with stannous chloride dihydrate (41.6 g, 184.5 mmol). The mixture was refluxed for 17 hours, evaporated to 300 ml and aqueous ammonia (S.G. 0.88) added to pH 10. The resulting suspension filtered, washed with ethyl acetate and evaporated to give a yellow oil which was purified by flash chromatography (ethyl acetate/ iso-hexane: 1/1) to give methyl 3-amino-6-(4-fluorobenzyl)benzoate (7.54 g; 85%)

$^1$H NMR (CDCl3, 300 MHz) δ3.65–3.68 (2H, broad); 3.77 (3H, s); 4.25 (2H, s); 6.71–6.73 (1H, d); 6.96–7.00 (1H, d); 7.10–7.26 (6H,m).

MS (CI$^+$) m/z 242 (MH$^+$)

MS (EI$^+$) m/z 241 (MH$^+$)

EXAMPLE 10

(2S)-2-{5-[1(4-Fluorophenyl)-2-(imidazol-1-yl)ethylamino]-2-(4-fluorobenzyl)benzoylamino}-4-methylsulfanylbutyric acid The title compound was prepared using a similar method to that of Example 1.

Yield: 68%

M.P.: 130–135° C.

$^1$H NMR (DMSO d$_6$+CF$_3$COOD, 400 MHz) δ: 1.9–2.1 (2H, m); 2.04 (3H, s); 2.4–2.55 (2H, m); 3.7–4.05 (2H, m); 4.4–4.55 (3H, m); 5.0 (1H, m); 6.49 (1H, m); 6.64 (1H, m); 6.88 (1H, m); 6.97 (2H, m); 7.1–7.2 (4H, m); 7.50 (2H, m); 7.63 (1H, m); 7.80 (1H, m); 9.06 (1H, s).

Anal. Calculated for C$_{30}$H$_{30}$F$_2$N$_4$O$_3$S, 1 H$_2$O

|  | C 61.84 | H 5.54 | N 9.62 | S 5.50 |
|---|---|---|---|---|
| Found | C 61.52 | H 5.34 | N 9.65 | S 5.17 |

MS (ESI) m/z 565 (MH$^+$)

EXAMPLE 11

N-Methylpiperidin-4-yl (2S)-2-{2-(4-fluorophenyl)-4-[1-(4-fluorophenyl)-2-(imidazol-1-yl)ethylamino]benzoylamino}-4-methylsulfanylbutyrate The title compound was prepared using a similar method to that of example 2, but using N-methylpiperidin-4-yl (2S)-2-amino-4-(methylsulfanyl)butanoate (L-methionine ( N-methylpiperidin-4-yl) ester) in place of L-methionine methyl ester.

Yield: 67%

$^1$H NMR (CDCl$_3$, 400 MHz) δ: 1.6–1.8 (4H, m); 1.8–2 (2H, m); 2.01 (3H, s); 2.1–2.3 (4H, m); 2.25 (3H, s); 2.57 (2H, s); 4.2–4.35 (3H, m); 4.5 (1H, m); 4.7–4.8 (2H, m): 5.78 (1H, m); 6.37(1H, m); 6.50 (1H, m); 6.76 (1H, m); 7–7.3 (10H, m); 7.50 (1H, m).

Anal. Calculated for C$_{35}$H$_{39}$F$_2$N$_5$O$_3$S, 0.5 H$_2$O

|  | C 64.01 | H 6.14 | N 10.66 | S 4.88 |
|---|---|---|---|---|
| Found | C 63.96 | H 6.14 | N 10.53 | S 4.64 |

MS (ESI) m/z: 648 (MH$^+$)

L-methionine (N-methylpiperidin-4-yl) ester was prepared as follows: A solution of tert-butoxycarbonyl-L-methionine (5 g; 20 mmol), 4-hydroxy-1-methylpiperidine (3.3 g; 20 mmol); DMAP (2.44 g; 20 mmol) and EDC (4.6 g; 2.4 mmol) in dichloromethane (200 ml) was stirred at ambient temperature overnight. The mixture was extracted with dichloromethane. The organic phase was evaporated and purified by flash chromatography, eluting with dichloromethane/ethanol (97/3) to give 1-methylpiperidin-4-yl-2-tert-butoxycarbonylamino-4-methylsulfanylbutyrate. Yield 56%.

$^1$H NMR (CDCl$_3$, 400 MHz) δ1.45 (9H, s); 1.6–2.2 (6H, m); 2.10 (3H, s); 2.2–2.4 (2H, m); 2.25 (3H, s); 2.4–2.75 (4H, m); 4.38 (1H, m) 4.85 (1H, m); 5.12 (1H, m).

A solution of the 1-methylpiperidin-4-yl 2-tert-butoxycarbonylamino-4-methylsulfanylbutyrate (3.8 g; 11 mmol) in dichloromethane (5 ml) and TFA (10 ml) was stirred at ambient temperature for 2 hours. After evaporation to dryness, the residue was redissolved in dichloromethane and treated with a solution of 3.8 M HCl in ether (6 ml) at 0° C. The resulting precipitate was triturated with ether and filtrated to give L-methionine (N-methylpiperidin-4-yl) ester.

$^1$H NMR (DMSO d$_6$+CF$_3$COOD, 400 MHz) δ1.8–2.2 (6H, m); 2.05 (3H, s); 2.45–2.9 (2H, m); 2.75 (3H, s); 3.25–3.5 (4H, m); 4.15 (1H, m); 4.9–5.1 (1H, m).

EXAMPLE 12

Tert-butyl (2S)-2-{2-(4-fluorophenyl)-4-[1-(4-fluorophenyl)-2-(imidazol-1-yl)ethylamino]benzoylamino}-4-methylsulfonylbutyrate A solution of tert-butyl (2S)-2-{2-(4-fluorophenyl)-4-[1-(4-fluorophenyl)-2-(imidazol-1-yl)ethylamino]benzoylamino}-4-methylsulfanylbutyrate (example 3) (0.45 g; 0.73 mmol) in dichloromethane (30 ml) and 60% MCPBA (0.53 g; 1.85 mmol) was stirred at room temperature for 3 hours. The mixture was washed with 1 M sodium thiosulfate, 5% sodium bicarbonate and saturated sodium chloride solution. After evaporation the residue was purified by flash chromatography (dichloromethane/ethanol 97/3) to give the title compound.

Yield: 61%

$^1$H NMR (CDCl$_3$, 400 MHz) δ: 1.40 (9H, s); 1.9–2.35 (2H, m); 2.7–2.95 (2H, m), 2.84(3H, s); 4.30 (2H, m); 4.4–4.5(2H, m); 4.7–4.8(1H, m); 5.9 (1H, m); 6.38 (1H, m), 6.50 (1H, s); 6.77 (1H, m); 7–7.3 (10 H, m); 7.48 (1H, m).

Anal. Calculated for $C_{33}H_{36}F_2N_4O_5S$

|  | | | | |
|---|---|---|---|---|
|  | C 62.05 | H 5.68 | N 8.77 | S 5.02 |
| Found | C 62.51 | H 6.44 | N 8.24 | S 4.54 |

MS (ESI) m/z: 639 (MH$^+$).

EXAMPLE 13

Methyl (2S)-2-{2-(4-fluorophenyl)-4-[1-(4-fluorophenyl)-2-(imidazol-1-yl)ethylamino]benzoylamino}-4-methylsulfonylbutyrate The title compound was prepared using a similar method to that of example 12, but oxidising example 2 instead of example 3.

Yield: 62%

$^1$H NMR (CDCl$_3$, 400 MHz) δ: 1.8–2.35 (2H, m); 2.7–3 (2H, m); 2.85 (3H, s); 3.72 (3H, s); 4.30 (2H, m); 4.40 (1H, m); 4.60 (1H, m); 4.75 (1H, m); 5.9 (1H, m); 6.39 (1H, m); 6.5 (1H, m); 6.80 (1H, s); 7–7.6 (11H, m).

Anal. Calculated for $C_{33}H_{30}F_2N_4O_5S$, 1 H$_2$O, 0.5 Et$_2$O

|  | | | | |
|---|---|---|---|---|
|  | C 58.97 | H 5.72 | N 8.60 | S 4.92 |
| Found | C 58.91 | H 5.36 | N 8.40 | S 4.45 |

MS (ESI) m/z: 597 (MH$^+$)

EXAMPLE 14

(2S)-2-{2-(4-Fluorophenyl)-4-[1-(4-fluorophenyl)-2-(imidazol-1-yl)ethylamino]benzoylamino}-methylsulfonylbutyric acid The title compound was prepared by deprotection of example 13, using a similar method to that of example 1.

Yield: 50%

$^1$H NMR (DMSOd$_6$+CF$_3$COOD) δ: 1.90–2.20 (2H, m); 2.8–3.15 (2H, m); 2.92 (3H, s); 4.21 (1H, m); 4.52 (2H, m); 5.15 (1H, m); 6.57 (2H, m); 7.05–7.35 (7H, m); 7.50 (2H, m); 7.65 (1H, m); 7.80 (1H, m); 9.06 (1H, s).

Anal. Calculated for $C_{29}H_{28}F_2N_4O_5S$, 1.8 H$_2$O

|  | | | | |
|---|---|---|---|---|
|  | C 56.63 | H 5.18 | N 9.11 | S 5.21 |
| Found | C 56.63 | H 5.28 | N 9.05 | S 5.02 |

MS (ESI) m/z: 583 (MH$^+$)

EXAMPLE 15

Tert-butyl (2S)-2-{2-(phenyl)-4-[1-(4-fluorophenyl)-2-(imidazol-1-yl)ethylamino]benzoylamino}-4-carbamoylbutyrate The title compound was prepared using a similar method to that of example 5, but using tert-butyl (2S)-2-amino-4-carbamoylbutanoate (L-glutamine tert-butyl ester) in place of the L-methionine methyl ester.

Yield: 18%

$^1$H NMR (CDCl$_3$, 400 MHz) δ: 1.33 (9H, s); 1.4–2.4 (4H, m); 4.29 (2H, m); 4.38 (2H, m); 4.76 (1H, m); 5.9 (1H, m); 6.42 (1H, m); 6.50 (1H, m); 6.76 (1H, s); 7–7.6 (12H, m).

|  | | | |
|---|---|---|---|
|  | C 65.66 | H 6.34 | N 11.6 |
| Found | C 65.79 | H 6.13 | N 11.47 |

MS (ESI=m/z: 586 (MH$^+$).

EXAMPLE 16

(2S)-2-{2-(Phenyl)-4-[1-(4-fluorophenyl)-2-(imidazol-1-yl)ethylamino]benzoylamino}-4-carbamoylbutyric acid A solution of compound tert-butyl (2S)-2-{2-(4-fluorophenyl)-4-[1-(4-fluorophenyl)-2-(imidazol-1-yl)ethylamino]benzoylamino})-4-carbamoylbutyrate (example 15) (0.09 g; 0.15 mmole) in TFA (3 ml) was stirred at room temperature for 30 minutes. After evaporation to dryness, the residue was purified on reverse phase silica, eluting with methanol/ammonium carbonate buffer (2 g /1, pH 7). The appropriate fractions were concentrated and freeze-dried to give the title compound.

Yield: 91%

$^1$H NMR (DMSO+CF$_3$COOD) δ: 1.8–2.2 (4H, m); 4.10 (1H, m); 4.52 (2H, m); 5.15 (1H,m); 6.55 (2H, m); 7.15–7.90 (12H, m); 8.1 (1H, d); 9.06 (1H, s).

Anal. Calculated for $C_{29}H_{28}FN_5O_4$, 1.7 H$_2$O

|  | | | |
|---|---|---|---|
|  | C 62.18 | H 5.65 | N 12.50 |
| Found | C 62.02 | H 5.33 | N 12.43 |

MS (ESI) m/z: 530 (MH$^+$)

EXAMPLE 17

Methyl (2S)-2-{2-(4-fluorobenzyl)-4-[1-(4-fluorophenyl)-2-(imidazol-1-yl)ethylamino]benzoylamino}-4-methylsulfanylbutyrate The title compound was prepared from 2-(4-fluorobenzyl)-4-[1-(4-fluorophenyl)-2-(imidazol-1-yl)ethylamino]benzoic acid using a similar method to that of example 2.

Yield: 26%.

$^1$H NMR (CDCl$_3$, 400 MHz) δ: 1.85–2.25 (2H, m); 2.1 (3H, s); 2.35–2.50 (2H, m); 3.73 (3H, s); 3.95–4.35 (4H, m); 4.6–4.8 (2H, m); 6.2–6.4 (2H, m); 6.72 (1H, s); 6.80–7.30 (12H, m).

Anal. Calculated for $C_{31}H_{32}N_4O_3SF_2$, 0.8 H$_2$O, 1.5 HCl

|  | | | | | |
|---|---|---|---|---|---|
|  | C 57.48 | H 5.46 | N 8.65 | S 4.95 | Cl 8.21 |
| Found | C 57.90 | H 5.49 | N 8.70 | S 4.76 | Cl 8.39 |

MS (ESI) m/z: 579 (MH$^+$).

EXAMPLE 18

(2S)-2-{2-(4-Fluorobenzyl)-4-[1-(4-fluorophenyl)-2-(imidazol-1-yl)ethylamino]benzoylamino}-4-methylsulfanylbutyric acid The title compound was prepared from example 17 using a similar method to that of example 1.

Yield: 60%

$^1$H NMR (DMSOd$_6$+CF$_3$COOD, 400 MHz) δ: 1.8–2.2 (2H, m); 2.02 (3H, s); 2.4–2.6 (2H, m); 3.8–4.2 (2H, m); 4.42 (1H, m); 4.50 (2H, m); 5.02 (1H, m); 6.4 (2H, m); 6.9–7.2 (7H, m); 7.4 (2H, m); 7.64 (1H, s); 7.78 (1H, s); 9.03 (1H, s).

Anal. Calculated for C$_{30}$H$_{30}$F$_2$N$_4$O$_3$S, 2 H$_2$O

|  | C 59.99 | H 5.71 | N 9.33 | S 5.34 |
|---|---|---|---|---|
| Found | C 59.61 | H 5.49 | N 9.16 | S 4.95 |

MS (ESI) m/z: 565 (MH$^+$)

EXAMPLE 19

Isopropyl (2S)-2-{5-[1-(4-fluorophenyl)-2-(imidazol-1-yl)ethylaminomethyl]-2(4-fluorobenzyl)benzoylamino}-4-methylsulfanylbutyrate A mixture of 5-[1-(4-fluorophenyl)-2-imidazol-1-yl) ethylaminomethyl]-2-(4-fluorobenzyl)benzoic acid (1.0 g), EDC(0.64 g), DMAP(2.2 g), L-methionine-isopropyl ester (2.5 g) and dichloromethane (30 ml) was stirred under an inert atmosphere for 16 hours, treated with 1 M. aqueous citric acid (30 ml), dried and applied directly to a silica flash column. Elution with ethyl acetate, ethyl acetate/methanol (95:5) and finally ethyl acetate/methanol (90:10) gave isopropyl (2S)-2-{5-[1-(4-fluorophenyl)-2-(imidazol-1-yl)ethylaminomethyl]-2-(4-fluorobenzyl)benzoylamino}-4-methylsulfanylbutyrate as a white foam. 0.6 g of this material was dissolved in ethyl acetate (20 ml) and treated with 1M ethereal HCl (30 ml) and the mixture diluted with more ether (100 ml) to give a white precipitate. The solid was isolated by centrifuging, washing with more ether, recentrifuging and then drying under high vacuum to give the hydrochloride salt of isopropyl (2S)-2-{5-[1-(4-fluorophenyl)-2-(imidazol-1-yl)ethylaminomethyl]-2-(4-fluorobenzyl)benzoylamino}-4-methylsulfanylbutyrate (0.59 g).

NMR data δ1.28(6H, t), 2.0(1H, m), 2.08(3H, s), 2.17(1H, m), 2.47(2H, m), 3.47(1H, 2d), 3.67(1H, d), 3.9(1H, d), 4.0–4.26(4H, m), 4.7(1H, q), 5.09(1H, m), 6.62(1H, 2d), 6.78(1H, s), 6.88–7.33(14H, m).

MS m/e 621.5 (M+H)$^+$

| Elemental Analysis found | C, 56.7; H, 5.8; N, 7.8; |
|---|---|
| +2HCl, 1H$_2$O | C, 57.3; H, 5.9; N, 7.87. |

The starting material was prepared as follows:

A 2.0M solution of 4-fluorobenzyl zinc bromide in tetrahydrofuran (95 ml, 190 mmol; Negishi, E-i. and King, A. O., J.O.C.1977,42,1821) was added dropwise over 20 minutes to a stirred solution of dimethyl 4-bromoisophthalate (20.0 g, 73.2 mmol) and tris(dibenzylideneacetone)dipalladium(O) (0.67 g,0.73 mmol) in tetrahydrofuran (270 ml) at ambient temperature under an inert atmosphere. During the addition the internal temperature rose to 40° C. The reaction mixture was stirred for 3 hours and then poured into 2M. HCl (1500 ml), cooled in an ice bath and the product extracted into ethyl acetate (3×700 ml). The extracts were washed with water (500 ml), brine (500 ml), dried, and the solvent evaporated under reduced pressure. The residue was taken up in a small quantity of dichloromethane, iso-hexane added, and the solid which crystallised from the solution, filtered and dried to give methyl 4-(4-fluorobenzyl)-3-methoxycarbonylbenzoate (10.5 g)

NMR data (CDCl$_3$) δ: 3.87 (3H, s), 3.95 (3H, s), 4.40 (2H, s), 6.93–7.00 (2H, m) 7.06–7.15 (2H, m), 7.29 (1H, d), 8.07 (1H, dd), 8.58 (1H, d).

MS m/e 303 (M+H)$^+$

Methyl 4-(4-fluorobenzyl)-3-methoxycarbonylbenzoate (16.9 g, 56.0 mmol) in methanol (270 ml) was warmed slightly to achieve solution. 2.5M Sodium hydroxide (27 ml,67.5 mmol) was added and the reaction mixture stirred at ambient temperature for 5 hours. The reaction mixture was poured into water (1200 ml), acidified with concentrated HCl and the product extracted into dichloromethane (3×400 ml). The combined extracts were washed with brine, dried and the solvent evaporated under reduced pressure to give a mixture of 4-(4-fluorobenzyl)-3-methoxycarbonylbenzoic acid and the isomeric monoester, as a cream solid (15.8 g).

NMR data (CDCl$_3$) δ: 3.85–3.98 (3H, m), 4.40–4.52 (2H, m), 6.94–7.02 (2H, m), 7.07–7.17(2H, m), 7.32–7.38 (1H, m), 8.15–8.19 (1H, m), 8.63–8.75 (1H, m)

MS m/e 287 (M–H)$^-$

A 1.0M solution of borane in tetrahydrofuran (100 ml, 100 mmol) was slowly added to a stirred solution of the monoester mixture (15.8 g, 54.7 mmol) at ambient temperature under an inert atmosphere. After the addition the reaction mixture was refluxed for 2 hours, cooled to ambient temperature and methanol (100 ml) added. The solvent was evaporated under reduced pressure and the product purified by column chromatography eluting with ethyl acetate/ isohexane (35:65 and 40:60) to give methyl 5-hydroxymethyl-2-(4-fluorobenzyl)benzoate as a light yellow oil (9.3 g).

NMR data (CDCl$_3$) δ: 1.82 (1H, t), 3.82 (3H, s), 4.35 (2H, s); 4.68–4.74 (2H, m), 6.90–6.99 (2H, m), 7.05–7.13 (2H, m), 7.21 (1H, d), 7.46 (1H, dd), 7.90 (1H, d)

MS mn/e 275 (M+H)$^+$

Triphenylphosphine (9.7 g., 37.0 mmol) and then carbon tetrabromide (12.3 g., 37.0 mmol) were added to a stirred solution of methyl 5-hydroxymethyl-2-(4-fluorobenzyl)benzoate (4.6 g., 16.8 mmol) in anhydrous ether (150 ml) at ambient temperature. After 4 hours the reaction was filtered and the filtrate concentrated under reduced pressure. The product was purified by column chromatography eluting with ethyl acetate/isohexane (5:95) to give methyl 5-bromomethyl-2-(4-fluorobenzyl)benzoate as a colourless oil (5.05 g).

NMR data (CDCl$_3$) δ: 3.83 (3H, s), 4.37 (2H, s), 4.50 (2H, s), 6.92–6.99 (2H, m) 7.06 7.13 (2H, m), 7.19 (1H, d). 7.43 (1H, dd), 7.95 (1H, d).

A mixture of methyl 5-bromomethyl-2-(4-fluorobenzyl)benzoate (3.8 g), sodium azide (2.9 g) and dimethyl acetamide (50 ml) was stirred under an inert atmosphere for 16 hours. The dimethyl acetamide was evaporated and the residue was partitioned between water and ethyl acetate. The organic layer was separated, dried, evaporated to dryness and purified by flash chromatography using iso-hexane/ethyl acetate (80:20) as eluant to give methyl 5-azidomethyl-2-(4-fluorobenzyl)benzoate (3.23 g) as a colourless gum.

NMR data δ3.82(3H, s), 4.34(2H, s), 4.37(2H, s), 6.92 (2H, m), 7.1(2H, m), 7.22(1H, m), 7.4(1H, m), 7.85(1H, d).

MS m/e 300.5 (M+H)$^+$

A mixture of methyl 5-azidomethyl-2-(4-fluorobenzyl) benzoate (3.23 g), 10% palladium on carbon (0.5 g), 1M. ethereal HCl (20 ml) and methanol (100 ml) was stirred under an atmosphere of hydrogen for 6 hours. The catalyst was filtered off and the filtrate was evaporated to dryness. The residue was treated with saturated aqueous sodium bicarbonate (100 ml) and extracted with ethyl acetate. The solution obtained was dried and evaporated to dryness to give methyl 5-aminomethyl-2-(4-fluorobenzyl)benzoate as a colourless gum (2.7 g).

MS m/e 274.4 (M+H)$^+$

A solution of 1-(4-fluorobenzoylmethyl)imidazole in dichloromethane (30 ml) was added to a mixture of methyl 5-aminomethyl-2-(4-fluorobenzyl)benzoate (2.7 g), sodium triacetoxyborohydride (3.5 g) 4A powdered molecular sieves (10 g) and dichloromethane, stirred and cooled to −20° C. under an inert atmosphere. After the addition was completed, the reaction was allowed to warm to ambient temperature and stirred for a further 16 hours. The molecular sieves were filtered off and the filtrate treated with saturated aqueous sodium bicarbonate solution (100 ml), separated, dried and applied directly to a silica flash column. Elution with ethyl acetate/iso-hexane (1:1), ethyl acetate and finally ethyl acetate/methanol (9:1) gave methyl 5-[1-(4-fluorophenyl)-2-(imidazol-1-yl)ethylaminomethyl]-2-(4-fluorobenzyl)benzoate as a colourless gum(1.5 g).

NMR data δ3.5+3.67(2H, 2d), 3.8(3H, s), 3.93(1H, m), 4.07(2H, m), 4.3(2H, s), 6.75(1H, s), 6.88–7.31(13H, m), 7.89(1H, s)

MS m/e 462.4 (M+H)$^-$

A mixture of methyl 5-[1-(4-fluorophenyl)-2-(imidazol-1-yl)ethylaminomethyl]-2-(4-fluorobenzyl)benzoate (1.5 g) sodium hydroxide (0.65 g), water (10 ml) and methanol (50 ml) was stirred under an inert atmosphere at ambient temperature for 2 hours. It was then acidified to pH 4–5 with 1M citric acid and evaporated to dryness. The residue was partitioned between ethyl acetate and water, the organic layer separated, treated with saturated brine, dried and evaporated to dryness to give 5-[1-(4-fluorophenyl)-2-(imidazol-1-yl)ethylaminomethyl]-2-(4-fluorobenzyl) benzoic acid as a white foam (1.0 g).

EXAMPLE 20

(2S)-2-{5-[1-(4-Fluorophenyl-2-(imidazol-1-yl) ethylaminomethyl]-2-(4-fluorobenzyl) benzoylamino}-4-methylsulfanylbutyric acid A mixture of isopropyl (2S)-2-{5-[1-(4-fluorophenyl)-2-(imidazol-1-yl)ethylaminomethyl]-2-(4-fluorobenzyl) benzoylamino}-4-methylsulfanylbutyrate (0.1 g), sodium hydroxide (0.129 g), water (2 ml) and methanol (10 ml) was stirred under an inert atmosphere for 3 hours. It was then acidified to pH 2 with 2M HCl , evaporated to dryness and water (1 ml) added to the gummy residue. The solution was removed and the residue washed with more water (0.5 ml). The gum obtained was dried under high-vacuum to give the title compound as a white solid (0.08 g).

NMR data δ2.05(2H, m), 2.12(3H, s), 2.55(2H, m), 3.56 (2H, m), 3.98–4.38(6H, m), 6.88 (1H, s), 7.08–7.52(13H, m), 7.91(1H, d).

MS m/e 577.3 (M–H)$^-$

Elemental Analysis found C, 57.1; H, 5.0; N, 8.6; +2HCl, 57.08; H, 5.06; N, 8.6.

EXAMPLE 21

Isopropyl (2S)-2-{5-[N-acetyl-1-(4-fluorophenyl)-2-(imidazo-1-yl)ethylaminomethyl]-2-(4-fluorobenzyl) benzoylamino}-4-methylsulfanylbutrate A mixture of isopropyl (2)-2-{5-[1-(4-fluorophenyl)-2-(imidazol-1-yl)ethylaminomethyl]-2-(4-fluorobenzyl) benzoylamino}-4-methylsulfanylbutyrate (0.2 g), triethylamine (0.23 ml), acetic anhydride (0.15 ml) and dichloromethane (10 ml) was stirred for 16 hours and then applied directly to a silica flash column. Elution with ethyl acetate/iso-hexane (1:1) and ethyl acetate/methanol (9:1) gave isopropyl (2S)-2-{5-[N-acetyl-1-(4-fluorophenyl)-2-(imidazol-1-yl)ethylaminomethyl]-2-(4-fluorobenzyl) benzoylamino}-4-methylsulfanylbutyrate as a white foam.

NMR data δ1.11(3H, t), 1.19(3H, t), 2.1(3H, s), 1.9–2.6 (7H, m), 3.08–3.42(5H, m), 3.93(2H, m), 4.55–4.8(1H. m), 5.0–5.3(1H, m), 6.2(1H, 2d), 6.75–7.41 (14H, m).

MS m/e 663.4 (M+H)$^+$

| | |
|---|---|
| Elemental Analysis found +0.5H$_2$O | C, 64.4; H, 5.9; N, 8.4; C, 64.3; H, 6.1; N, 8.3. |

EXAMPLE 22

(2S)-2-{2-(4-Fluorophenethyl)-5-[1-(4-fluorophenyl)-2-(imidazol-1-yl)ethylaminomethyl] benzoylamino}-4-methylsulfanylbutyric acid This was synthesised by the method used to prepare (2S)-2-{5-[1-(4-fluorophenyl)-2-(imidazol-1-yl) ethylaminomethyl]-2-(4-fluorobenzyl)benzoylamino}-4-methylsulfanylbutyric acid.

NMR data δ2.05(3H, s), 2.05(2H, m), 2.6(2H, m), 2.8(2H, m), 2.96(2H, m), 3.83+4.0(2H, 2d), 4.53(1H, m), 4.8(1H, m), 4.96(1H, m)5.16(1H, 2d), 7.0–7.9(15H,m).

MS m/e 591.3 (M–H)$^-$

The starting material for (2S)-2-{2-(4-fluorophenethyl)-5-[1-(4-fluorophenyl)-2-(imidazol-1-yl)ethylaminomethyl] benzoylamino}-4-methylsulfanylbutyric acid was prepared as follows:

A mixture of dimethyl 4-bromoisophthalate (54.75 g., 200.5 mmol), water (330 ml), tributylamine (55.63 g., 300.7 mmol), 4-fluorostyrene (55.63 g., 300.7 mmol) and bis (triphenylphoshine)palladium(II)chloride (2.81 g., 4.01 mmol) was heated at reflux with stirring under an inert atmosphere for 6 hours. The reaction was cooled to ambient temperature and acidified to pH 2 with 2M HCl (700 ml). The aqueous layer was removed and the residual solid washed with water (2 L), dissolved in dichloromethane (1 L) and passed through a pad of silica, eluting with more dichloromethane (2 L). Evaporation of the dichloromethane gave a solid, which was further washed with iso-hexane(1 L), and dried to give methyl 4-[2-4-fluorophenyl)ethenyl]-3-methoxycarbonylbenzoate (56.75 g) as a pale yellow solid.

NMR data (CDCl$_3$) δ: 3.96 (6H, 2s), 7.01–7.10 (3H, m), 7.49–7.57 (2H, m), 7.80 (1H, d), 7.97 (1H, d), 8.16 (1H, dd), 8.60 (1H, s).

MS m/e 315.3 (M+H)+.

A mixture of methyl 4-[2-(4-fluorophenyl)ethenyl]-3-methoxycarbonylbenzoate (56.75 g, 180.6 mmol), ethyl acetate (900 ml), 10% palladium on carbon (6 g) was stirred under an hydrogen atmosphere for 6 hours. The catalyst was filtered and replaced with fresh catalyst (6 g). The reaction was then stirred under an hydrogen atmosphere for 16 hours. The catalyst was filtered and the filtrate evaporated to dryness to give as a colourless gum, methyl 4-(4-fluorophenethyl)-3-methoxycarbonylbenzoate (55.00 g).

NMR data (CDCl$_3$) δ: 2.84–2.93 (2H, m), 3.25–3.33 (2H, m), 3.93 (6H, 2s), 6.90–7.00 (2H, m), 7.09–7.16 (2H, m), 7.22–7.28 (1H, m), 8.05 (1H, dd), 8.57 (1H, s).

MS m/e 317.3 (M+H)+.

A mixture of methyl 4-(4-fluorophenethyl)-3-methoxycarbonylbenzoate (51.00 g., 161.22 mmol), dioxane (650 ml), methanol (650 ml), sodium hydroxide (7.10 g., 177.35 mmol) and water (100 ml) was stirred at ambient temperature under an inert atmosphere for 16 hours. The reaction was evaporated to dryness, water (500 ml) was added to the residue and the mixture extracted with diethyl ether. The organic extracts were dried and evaporated to dryness to give recovered methyl 4-(4-fluorophenethyl)-3-methoxycarbonylbenzoate (7 g). The aqueous layer was acidified to pH 2 with 2M HCl (300 ml) and extracted with ethyl acetate (300 ml). The organic extracts were dried, filtered and evaporated to dryness to give as a white solid 4-(4-fluorophenethyl)-3-methoxycarbonylbenzoic acid (42.00 g).

NMR data (DMSO d$_6$) δ: 2.77–2.85 (2H, m), 3.16–3.24 (2H, m), 3.85 (3H, s), 7.04–7.12 (2H, m), 7.17–7.25 (2H, m), 7.45 (1H, d), 8.00 (1H, dd), 8.535 (1H, s).

MS m/e 301.4 (M−H)−.

A mixture of 4-(4-fluorophenethyl)-3-methoxycarbonylbenzoic acid (16.5 g, 54.88 mmol), tetrahydrofuran (500 ml) and borane in tetrahydrofuran (1 M. complex, 218 ml, 218 mmol) was stirred under an inert atmosphere at reflux for 6 hours. The reaction was cooled to ambient temperature and methanol (1 L) was added. It was then evaporated to dryness to give a dark oil which was purified by flash chromatography using iso-hexane/ethyl acetate (1:1) as eluant to give as a clear gum methyl 2-(4-fluorophenethyl)-5-hydroxymethylbenzoate (13.10 g).

NMR data (CDCl$_3$) δ: 1.74 (1H, t), 2.82–2.92 (2H, m), 3.17–3.27 (2H, m), 3.91 (3H, s), 4.71 (2H, d), 6.91–6.99 (2H, m), 7.11–7.20 (3H, m), 7.41 (1H, d), 7.91 (1H, s).

MS m/e 289 (M+H)+.

A mixture of methyl 2-(4-fluorophenethyl)-5-hydroxymethylbenzoate (13.10 g., 45.43 mmol), carbon tetrabromide (18.08 g, 54.52 mmol) and triphenylphosphine (14.30 g, 54.52 mmol) in dichloromethane (400 ml) was stirred at ambient temperature for 4 hours. More carbon tetrabromide (7.54 g, 23.00 mmol) and triphenylphosphine (5.96 g, 23.00 mmol) in dichloromethane (50 ml) were added and then stirred for a further 2 hours. The reaction was applied directly to a silica flash column and eluted with iso-hexane/ethyl acetate (92.5:7.5) to give as a clear gum methyl 2-(4-fluorophenethyl)-5-bromomethylbenzoate (9.30 g).

NMR data (CDCl$_3$) δ: 2.81–2.91 (2H, m), 3.19–3.27 (2H, m), 3.91 (3H, s), 4.48 (2H, s), 6.91–7.00 (2H, m), 7.12–7.17 (3H, m), 7.44 (1H, dd), 7.95 (1H, s).

MS m/e's 351 and 353 (M+H)+.

EXAMPLE 23

Isopropyl (2S)-2-{2-(4-fluorophenethyl)-5-[1-(4-fluorophenyl)-2-imidazol-1-yl)ethylaminomethyl]benzoylamino}-4-methylsulfanylbutyrate The title compound was prepared from methyl 2-(4-fluorophenethyl)-5-bromomethylbenzoate by the route described for the preparation of isopropyl (2S)-2-{5-[1-(4-fluorophenyl-2-(imidazol-1-yl)ethylaminomethyl]-2-(4-fluorobenzyl)benzoylamino}-4-methylsulfanylbutyrate from methyl 5-bromomethyl-2-(4-fluorobenzyl)benzoate.

NMR data δ1.28(6H, t), 2.1(3H, s), 2.12(1H, m), 2.28(1H, m), 2.6(2H, t); 2.88(2H, t), 3.02(2H, m),3.43+3.68(2H, 2d), 3.9(1H, m), 4.03(2H, d), 4.83(1H, m),5.1(1H, m), 6.7(1H, 2d), 6.78(1H, s), 6.92(2H, t), 7.0–7.32(12H, m).

MS m/e 635.5 (M+H)+

The starting material was prepared as follows:

Methyl 2-(4-fluorophenethyl)-5-azidomethylbenzoate:

NMR data, δ2.86(2H, t), 3.22(2H, t), 3.91(3H, s), 4.36 (2H, s), 6.94(2H, t), 7.14(3H, m), 7.36(1H, 2d), 7.87(1H, d).

MS m/e 314.5 (M+H)+

Methyl 2-(4-fluorophenethyl)-5-aminomethylbenzoate:

MS m/e 288.4 (M+H)+

Methyl 2-(4-fluorophenethyl)-5-[1-(4-fluorophenyl)-2-(imidazol-1-yl)ethylaminomethylbenzoate:

NMR data δ2.86(2H, t), 3.2(2H, t), 3.5+3.7(2H, 2d), 3.9(3H, s), 4.0(3H, m), 6.88–7.48(15H, m)

MS m/e 476.5 (M+H)+

What is claimed is:

1. A compound of Formula (1):

Formula (1)

$$\text{Ar}^1\text{C}(\text{R}^{12})\text{R}^{13}$$

with structure containing Ar$^2$, N-R$^1$, (CH$_2$)$_p$-Ar$^3$ wherein Ar$^1$ represents:

(A), (B), (C) — imidazole/pyrazole ring structures with (R$^6$)$_m$, R$^5$, R$^6$ substituents R$^5$ is hydrogen, C$_{1-4}$alkyl, phenylC$_{1-4}$alkyl;
R$^6$ is hydrogen, C$_{1-4}$alkyl, hydroxyC$_{1-4}$alkyl, haloC$_{1-4}$alkyl, dihaloC$_{1-4}$alkyl, C$_{1-4}$alkoxy, C$_{1-4}$alkoxyC$_{1-4}$alkyl, sulfanylC$_{1-4}$alkyl, aminoC$_{1-4}$alkyl, N—(C$_{1-4}$alkyl)aminoC$_{1-4}$alkyl, N,N-di-(C$_{1-4}$alkyl)aminoC$_{1-4}$alkyl or phenylC$_{1-4}$alkyl; m is 0, 1 or 2;
R$^1$ is hydrogen, C$_{1-4}$alkyl or C$_{1-4}$alkanoyl;
R$^{12}$ and R$^{13}$ are independently hydrogen or C$_{1-4}$alkyl;
Ar$^2$ is phenyl or heteroaryl;
p is 0 or 1;
Ar$^3$ is of the formula:

ring structure with W, X$^3$, R$^2$, Y$^5$, Z, (CH$_2$)$_n$R$^3$ wherein W, X, Y and Z are independently is CH or N, provided that at least two of W, X, Y and Z are CH and $R^2$ and —$(CH_2)_nR^3$ are attached to ring carbon atoms;

$R^2$ is a group of the Formula (2):

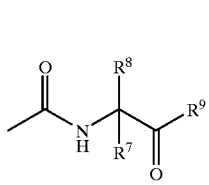

Formula (2)

wherein $R^7$ is hydrogen or $C_{1-4}$alkyl, $R^8$ is —$(CH_2)_q$—$R^{10}$ wherein q is 0–4 and $R^{10}$ is $C_{1-4}$alkylsulfanyl, $C_{1-4}$alkylsulfinyl, $C_{1-4}$alkylsulfonyl, hydroxy, $C_{1-4}$alkoxy, carbamoyl, $\underline{N}$—$C_{1-4}$alkylcarbamoyl, $\underline{N,N}$-(di$C_{1-4}$alkyl)carbamoyl, $C_{1-4}$alkyl, phenyl, thienyl, or $C_{1-4}$alkanoylamino; $R^9$ is hydroxy, $C_{1-6}$alkoxy, $C_{3-9}$cycloalkyloxy, heterocyclyloxy, heterocyclyl$C_{1-4}$alkoxy or —NH—$SO_2$—$R^{11}$ wherein $R^{11}$ represents, trifluoromethyl, $C_{1-4}$alkyl, phenyl, heteroaryl, aryl$C_{1-4}$alkyl or heteroaryl$C_{1-4}$alkyl;

or $R^2$ represents a lactone of Formula (3)

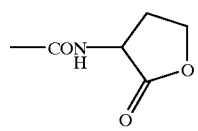

Formula (3)

the group of Formula (2) or (3) having L or D configuration at the chiral alpha carbon in the corresponding free amino acid;

n is 0, 1 or 2;

$R^3$ is phenyl or heteroaryl;

phenyl and heteroaryl rings in $R^3$, $R^5$, $R^6$, $R^9$, $R^{11}$ and $Ar^2$ are independently optionally substituted on ring carbon atoms by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, thiol, $C_{1-4}$alkylsulfanyl, $C_{1-4}$alkylsulfinyl, $C_{1-4}$alkylsulfonyl, $C_{1-4}$alkanesulphonamido, $\underline{N}$-($C_{1-4}$alkylsulphonyl)-$\underline{N}$—$C_{1-4}$alkylamino, aminosulfonyl, $\underline{N}$-($C_{1-4}$alkyl)aminosulfonyl, $\underline{N,N}$-di($C_{1-4}$alkyl)aminosulfonyl, carbamoyl, $\underline{N}$—($C_{1-4}$alkyl)carbamoyl, $\underline{N,N}$-(di$C_{1-4}$alkyl)carbamoyl, carbamoyl$C_{1-4}$alkyl, $\underline{N}$—($C_{1-4}$alkyl)carbamnoyl$C_{1-4}$alkyl, $\underline{N,N}$-(di$C_{1-4}$alkyl)carbamoyl$C_{1-4}$alkyl, hydroxy$C_{1-4}$alkyl and $C_{1-4}$alkoxy$C_{1-4}$alkyl and on ring NH groups by $C_{1-4}$alkyl, $C_{1-4}$alkanoyl, $C_{1-4}$alkylsulfonyl, halo$C_{1-4}$alkyl, difluoromethyl or trifluoromethyl;

wherein, in each of $Ar^2$, $R^2$ and $R^3$, each said heterocyclyl group is a 5- or 6-membered monocyclic ring containing 1 to 3 heteroatoms selected from nitrogen, oxygen and sulfur;

and each said heteroaryl group is a 5–10 membered monocyclic heteroaryl ring containing up to 3 heteroatoms selected from nitrogen, oxygen and sulphur;

provided that:

when n is 0, $Ar^3$ is substituted by $R^2$ in the 4-position and —$(CH_2)_nR^3$ in the 3- or 5-position; and when n is 1 or 2, $Ar^3$ is substituted by $R^2$ in the 3- or 5-position and —$(CH_2)_nR^3$ in the 4-position;

or a pharmaceutically acceptable salt, prodrug or solvate thereof.

2. A compound according to claim 1 wherein $Ar^1$ is of the formula (A) or (B):

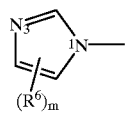

(A)

or

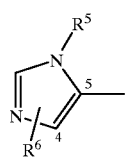

(B)

wherein $R^5$ is hydrogen or methyl; $R^6$ is hydrogen, $C_{1-4}$alkyl, hydroxy$C_{1-4}$alkyl, amino$C_{1-4}$alkyl, fluoro$C_{1-4}$alkyl, difluoro$C_{1-4}$alkyl, $C_{1-4}$alkoxy or $C_{1-4}$alkoxy$C_{1-4}$alkyl and m is as defined in claim 1.

3. A compound according to either claim 1 or claim 2 wherein $Ar^2$ is phenyl, thiazolyl, pyridyl, triazolyl, pyrimidyl, pyrazinyl or pyridazinyl optionally substituted on ring carbon atoms by $C_{1-4}$alkyl, halo, nitro, cyano or $C_{1-4}$alkoxy$C_{1-4}$alkyl.

4. A compound according to either claim 1 or claim 2 wherein $Ar^2$ is phenyl or thiazolyl optionally substituted on ring carbon atoms by $C_{1-4}$alkyl, halo, nitro, cyano or $C_{1-4}$alkoxy$C_{1-4}$alkyl.

5. A compound according to either claims 1 or claim 2 wherein at least three of W, X, Y and Z in $Ar^3$ are CH.

6. A compound according to either claims 1 or claim 2 wherein $R^1$ is hydrogen, methyl or acetyl.

7. A compound according to either claims 1 or claim 2 wherein $R^2$ is of the formula (2):

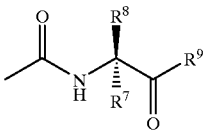

wherein $R^7$ is hydrogen or methyl;

$R^8$—$(CH_2)_q$—$R^{10}$ wherein q is 1 or 2; $R^{10}$ is $C_{1-4}$alkylsulfanyl, $C_{1-4}$alkylsulfinyl, $C_{1-4}$alkylsulfonyl, hydroxy or $C_{1-4}$alkoxy;

$R^9$ is hydroxy, $C_{1-4}$alkoxy, $C_{3-9}$cycloalkyloxy, heterocyclyloxy or heterocyclyl$C_{1-4}$alkoxy or of the formula —$NHSO_2R^{11}$ wherein $R^{11}$ is phenyl; wherein NH groups in heterocyclic groups in $R^9$ are optionally substituted by methyl, ethyl, acetyl, propionyl, fluoromethyl, difluoromethyl or trifluoromethyl and ring carbon atoms in phenyl or heteroaryl groups in $R^{11}$ are optionally substituted by methyl, halo, $C_{1-4}$alkanoyl, nitro, cyano, $C_{1-4}$alkylsulfinyl, $C_{1-4}$alkylsulfonyl, carbamoyl, $C_{1-4}$alkylcarbamoyl or di$C_{1-4}$alkylcarbamoyl;

or wherein $R^2$ is of the formula (3) as defined in claim 1.

8. A compound according to either claims 1 or claim 2 wherein $R^3$ is phenyl, pyridyl or thiazolyl and ring carbon atoms in $R^3$ are optionally substituted by $C_{1-4}$alkyl, halo, $C_{1-4}$alkoxy, nitro, cyano or $C_{1-4}$alkoxy$C_{1-4}$alkyl and a ring NH group in a heteroaryl group in $R^3$ is optionally substituted by $C_{1-4}$alkyl.

9. A compound according to either claims 1 or claim 2 wherein $R^{11}$ and $R^{12}$ are independently hydrogen or methyl.

10. A compound which is:

(2S)-2-{2-(4-fluorophenyl)-4-[1-(4-fluorophenyl)-2-imidazol-1-yl)ethylamino]benzoylamino}-4-methylsulfanylbutyric acid;

methyl(2S)-2-{2-(4-fluorophenyl)-4-[1-(4-fluorophenyl)-2-(imidazol-1-yl)ethylamino]benzoylamino}-4-methylsulfanylbutyrate;

tert-butyl(2S)-2-{2-(4-fluorophenyl)-4-[1-(4-fluorophenyl)-2-(imidazol-1-yl)ethylamino]benzoylamino}-4-methylsulfanylbutyrate;

N-propanesulphonyl (2S)-2-{2-(4-fluorophenyl)-4-[1-(4-fluorophenyl)-2-(imidazol-1-yl)ethylamino]benzoylamino}-4-methylsulfanylbutyramide;

methyl(2S)-2-{2-phenyl-4-[1-(4-fluorophenyl)-2-(imidazol-1-yl)ethylamino]benzoylamino}-4-methylsulfanylbutyrate;

(2S)-2-{2-phenyl-4-[1-(4-fluorophenyl)-2-imidazol-1-yl)ethylamino]benzoylamino}-4-methylsulfanylbutyric acid;

methyl(2S)-2-{5-[1-(4-fluorophenyl)-2-imidazol-1-yl)ethylamino]-2-(4-fluorophenethyl)benzoylamino}-4-methylsulfanylbutyrate;

(2S)-2-{5-[1-(4-fluorophenyl)-2-(imidazol-1-yl)ethylamino]-2-(4-fluorophenylethyl)benzoylaminoamino}-4-methylsulfanylbutyric acid;

methyl(2S)-2-{5[1-(4-fluorophenyl)-2-imidazol-1-yl)ethylamino]-2-(4-fluorobenzyl)benzoylamino}-4-methylsulfanylbutyrate;

(2S)-2-{5-[1-(4-fluorophenyl)-2-(imidazol-1-yl)ethylamino]-2-(4-fluorobenzyl)benzoylamino}-4-methylsulfanylbutyric acid;

isopropyl(2S)-2-{5-[1-(4-fluorophenyl)-2-(imidazol-1-yl)ethylaminoethyl]-2-(4-fluorobenzyl)benzoylamino)}-4-methylsulfanylbutyrate;

(2S)-2-{5-[1-(4-fluorophenyl)-2-imidazol-1-yl)ethylaminomethyl]-2-(4-fluorobenzyl)benzoylamino}-4-methylsulfanylbutyric acid;

isopropyl(2S)-2-{5-[N-acetyl-1-(4-fluorophenyl)-2-(imidazol-1-yl)ethylaminomethyl]-2-4-fluorobenzyl)benzoylamino}-4-methylsulfanylbutyrate;

(2S)-2-{2-(4-fluorophenethyl)-5-[-1-(4-fluorophenyl)-2-(imidazol-1-yl)ethylaminomethyl]benzoylamino}-4-methylsulfanylbutyric acid;

isopropyl(2S)-2-{2-(4-fluorophenylethyl)-5-[1-(4-fluorophenyl)-2-(imidazol-1-yl)ethylaminomethyl]benzoylamino}-4-methylsulfanylbutyrate;

N-methylpiperidin-4-yl(2S)-2-{2-(4-fluorophenyl)-4-[1-(4-fluorophenyl)-2-imidazol-1-yl)ethylamino]benzoylamino}-4-methylsulfanylbutyrate;

tert-butyl(2S)-2-{2-(4-fluorophenyl)-4-[1-(4-fluorophenyl)-2-imidazol-1-yl)ethylamino]benzoylamino}-4-methylsulfonylbutyrate;

methyl(2S)-2-{2-(4-fluorophenyl)-4-[1-(4-fluorophenyl)-2-(imidazol-1-yl)ethylamino]benzoylamino}-4-methylsulfonylbutyrate;

(2S)-2-{2-(4-fluorophenyl)-4-[1-(4-fluorophenyl)-2-(imidazol-1-yl)ethylamino]benzoylamino}-4-methylsulfonylbutyric acid;

tert-butyl(2S)-2-{2-(phenyl)-4-[1-(4-fluorophenyl)-2-(imidazol-1-yl)ethylamino]benzoylamino}-4-carbamoylbutyrate;

(2S)-2-{2-(phenyl)-4-[1-(4-fluorophenyl)-2-(imidazol-1-yl)ethylamino]benzoylamino}-4-carbamoylbutyric acid;

methyl(2S)-2-{2-(4-fluorobenzyl)-4-[1-(4-fluorophenyl)-2-(imidazol-1-yl)ethylamino]benzoylamino}-4-methylsulfanylbutyrate; or (2S)-2-{2-(4-fluorobenzyl)-4-[1-(4-fluorophenyl)-2-(imidazol-1-yl)ethylamino]benzoylamino}-4-methylsulfanylbutyric acid;

or a pharmaceutically acceptable salt thereof.

11. A pharmaceutical composition which comprises a compound according to either claims 1 or 2 and a pharmaceutically-acceptable carrier.

12. A method of treating a disease or medical condition mediated through farnesylation of ras which comprises administering to a warm-blooded animal an effective amount of a compound according to either claims 1 or 2.

* * * * *